United States Patent
Baughn et al.

(10) Patent No.: US 7,122,362 B2
(45) Date of Patent: Oct. 17, 2006

(54) PHOSPHODIESTERASES

(76) Inventors: Mariah R. Baughn, 14244 Santiago Rd., San Leandro, CA (US) 94577; Dyung Aina M. Lu, 233 Coy Dr., San Jose, CA (US) 95123; Henry Yue, 826 Lois Ave., Sunnyvale, CA (US) 94087; Y. Tom Tang, 4230 Ranwick Ct., San Jose, CA (US) 95118; Danniel B. Nguyen, 4922 Amica Ct., San Jose, CA (US) 95111

( * ) Notice: Subject to any disclaimer, the term of this patent is extended or adjusted under 35 U.S.C. 154(b) by 615 days.

(21) Appl. No.: 10/182,324

(22) PCT Filed: Jan. 26, 2001

(86) PCT No.: PCT/US01/02649

§ 371 (c)(1),
(2), (4) Date: Jul. 26, 2002

(87) PCT Pub. No.: WO01/55358

PCT Pub. Date: Aug. 2, 2001

(65) Prior Publication Data

US 2003/0207434 A1 Nov. 6, 2003

Related U.S. Application Data

(60) Provisional application No. 60/183,178, filed on Feb. 17, 2000, provisional application No. 60/182,042, filed on Feb. 11, 2000, and provisional application No. 60/178,570, filed on Jan. 28, 2000.

(51) Int. Cl.
C12N 9/14 (2006.01)
C12N 9/16 (2006.01)
C12N 1/20 (2006.01)
C12N 15/00 (2006.01)
C07H 21/04 (2006.01)

(52) U.S. Cl. ............ 435/195; 435/196; 435/252.3; 435/320.1; 435/18; 435/21; 536/23.2

(58) Field of Classification Search .......... 435/195, 435/196, 252.3, 320.1; 536/23.2
See application file for complete search history.

(56) References Cited

FOREIGN PATENT DOCUMENTS

| WO | WO 99 33916 | 8/1998 |
|---|---|---|
| WO | WO 99/47540 | 12/1999 |

OTHER PUBLICATIONS

Attwood et al. Comput. Chem. 2001, col. 54(4), pp. 329–339.*

Ponting [Brief. Bioinform. Mar. 2001, vol. 2(1), pp. 19–29].*

[Accession No. AAZ65056] and Seq Id No. 4 alignment (WO 9963088–A2).*

[Accession No. AAY66716] and Seq Id No.: 1 alignment (WO 9963088–A2).*

NCBI Database, Accession BC027615 (GI 34190207), Nov. 12, 2002.

* cited by examiner

*Primary Examiner*—Tekchand Saidha
(74) *Attorney, Agent, or Firm*—Foley & Lardner

(57) ABSTRACT

The invention provides human phosphodiesterases (HPDE) and polynucleotides which identify and encode HPDE. The invention also provides expression vectors, host cells, antibodies, agonists, and antagonists. The invention also provides methods for diagnosing, treating, or preventing disorders associated with aberrant expression of HPDE.

12 Claims, No Drawings

PHOSPHODIESTERASES

This application is the National Stage of International Application No. PCT/US01/02649, filed on Jan. 26, 2001, which claims the benefit under 35 U.S.C. §119(e) of U.S. Provisional Application Ser. No. 60/178,570, filed Jan. 28, 2000, and claims the benefit of U.S. Provisional Application Ser. No. 60/182,042, filed Feb. 11, 2000, and claims the benefit of U.S. Provisional Application Ser. No. 60/183,178, filed Feb. 17, 2000, the contents all of which are hereby incorporated herein by reference.

TECHNICAL FIELD

This invention relates to nucleic acid and amino acid sequences of phosphodiesterases and to the use of these sequences in the diagnosis, treatment, and prevention of eye, neurological, cardiovascular, cell proliferative, and autoimmune/inflammatory disorders, and in the assessment of the effects of exogenous compounds on the expression of nucleic acid and amino acid sequences of phosphodiesterases.

BACKGROUND OF THE INVENTION

Phosphodiesterases make up a class of enzymes which catalyze the hydrolysis of one of the two ester bonds in a phosphodiester compound. Phosphodiesterases are therefore crucial to a variety of cellular processes. Phosphodiesterases include DNA and RNA endonucleases and exonucleases, which are essential for cell growth and replication, and topoisomerases, which break and rejoin nucleic acid strands during topological rearrangement of DNA. A Tyr-DNA phosphodiesterase functions in DNA repair by hydrolyzing dead-end covalent intermediates formed between topoisomerase I and DNA (Pouliot, J. J. et al. (1999) Science 286:552–555; Yang, S.- W. (1996) Proc. Natl. Acad. Sci. USA 93:11534–11539).

Acid sphingomyelinase is a phosphodiesterase which hydrolyzes the membrane phospholipid sphingomyelin to produce ceramide and phosphorylcholine. Phosphorylcholine is used in the synthesis of phosphatidylcholine, which is involved in numerous intracellular signaling pathways, while ceramide is an essential precursor for the generation of gangliosides, membrane lipids found in high concentration in neural tissue. Defective acid sphingomyelinase leads to a build-up of sphingomyelin molecules in lysosomes, resulting in Niemann-Pick disease (Schuchman, E. H. and S. R. Miranda (1997) Genet. Test. 1:13–19).

Glycerophosphoryl diester phosphodiesterase (also known as glycerophosphodiester phosphodiesterase) is a phosphodiesterase which hydrolyzes deacetylated phospholipid glycerophosphodiesters to produce sn-glycerol-3-phosphate and an alcohol. Glycerophosphocholine, glycerophosphoethanolamine, glycerophosphoglycerol, and glycerophosphoinositol are examples of substrates for glycerophosphoryl diester phosphodiesterases. A glycerophosphoryl diester phosphodiesterase from *E. coli* has broad specificity for glycerophosphodiester substrates (Larson, T. J. et al. (1983) J. Biol. Chem. 248:5428–5432).

Cyclic nucleotide phosphodiesterases (PDEs) are crucial enzymes in the regulation of the cyclic nucleotides cAMP and cGMP. cAMP and cGMP function as intracellular second messengers to transduce a variety of extracellular signals including hormones, light, and neurotransmitters. PDEs degrade cyclic nucleotides to their corresponding monophosphates, thereby regulating the intracellular concentrations of cyclic nucleotides and their effects on signal transduction. Due to their roles as regulators of signal transduction, PDEs have been extensively studied as chemotherapeutic targets (Perry, M. J. and G. A. Higgs (1998) Curr. Opin. Chem. Biol. 2:472–481; Torphy, J. T. (1998) Am. J. Resp. Crit. Care Med. 157:351–370).

Cyclic Nucleotide Phosphodiesterase Families

Families of mammalian PDEs have been classified based on their substrate specificity and affinity, sensitivity to cofactors, and sensitivity to inhibitory agents (Beavo, J. A. (1995) Physiol. Rev. 75:725–748; Conti, M. et al. (1995) Endocrine Rev. 16:370–389). Several of these families contain distinct genes, many of which are expressed in different tissues as splice variants. Within PDE families, there are multiple isozymes and multiple splice variants of these isozymes (Conti, M. and S.-L. C. Jin (1999) Prog. Nucleic Acid Res. Mol. Biol. 63:1–38). The existence of multiple PDE families, isozymes, and splice variants is an indication of the variety and complexity of the regulatory pathways involving cyclic nucleotides (Houslay, M. D. and G. Milligan (1997) Trends Biochem. Sci. 22:217–224).

Type 1 PDEs (PDE 1s) are $Ca^{2+}$/calmodulin-dependent and appear to be encoded by at least three different genes, each having at least two different splice variants (Kakkar, R. et al. (1999) Cell Mol. Life Sci. 55:1164–1186). PDE1s have been found in the lung, heart, and brain. Some PDE1 isozymes are regulated in vitro by phosphorylation/dephosphorylation. Phosphorylation of these PDE1 isozymes decreases the affinity of the enzyme for calmodulin, decreases PDE activity, and increases steady state levels of cAMP (Kakkar, supra). PDE1s may provide useful therapeutic targets for disorders of the central nervous system, and the cardiovascular and immune systems due to the involvement of PDE1s in both cyclic nucleotide and calcium signaling (Perry, M. J. and G. A. Higgs (1998) Curr. Opin. Chem. Biol. 2:472–481).

PDE2s are cGMP-stimulated PDEs that have been found in the cerebellum, neocortex, heart, kidney, lung, pulmonary artery, and skeletal muscle (Sadhu, K. et al. (1999) J. Histochem. Cytochem. 47:895–906). PDE2s are thought to mediate the effects of cAMP on catecholamine secretion, participate in the regulation of aldosterone (Beavo, supra), and play a role in olfactory signal transduction (Juilfs, D. M. et al. (1997) Proc. Natl. Acad. Sci. USA 94:3388–3395).

PDE3s have high affinity for both cGMP and cAMP, and so these cyclic nucleotides act as competitive substrates for PDE3s. PDE3s play roles in stimulating myocardial contractility, inhibiting platelet aggregation, relaxing vascular and airway smooth muscle, inhibiting proliferation of T-lymphocytes and cultured vascular smooth muscle cells, and regulating catecholamine-induced release of free fatty acids from adipose tissue. The PDE3 family of phosphodiesterases are sensitive to specific inhibitors such as cilostamide, enoximone, and lixazinone. Isozymes of PDE3 can be regulated by cAMP-dependent protein kinase, or by insulin-dependent kinases (Degerman, E. et al. (1997) J. Biol. Chem. 272:6823–6826).

PDE4s are specific for cAMP; are localized to airway smooth muscle, the vascular endothelium, and all inflammatory cells; and can be activated by cAMP-dependent phosphorylation. Since elevation of cAMP levels can lead to suppression of inflammatory cell activation and to relaxation of bronchial smooth muscle, PDE4s have been studied extensively as possible targets for novel anti-inflammatory agents, with special emphasis placed on the discovery of asthma treatments. PDE4 inhibitors are currently undergoing clinical trials as treatments for asthma, chronic obstructive pulmonary disease, and atopic eczema. All four known isozymes of PDE4 are susceptible to the inhibitor rolipram, a compound which has been shown to improve behavioral memory in mice (Barad, M. et al. (1998) Proc. Natl. Acad. Sci. USA 95:15020–15025). PDE4 inhibitors have also been studied as possible therapeutic agents against acute lung injury, endotoxemia, rheumatoid arthritis, multiple sclerosis, and various neurological and gastrointestinal indications (Doherty, A. M. (1999) Curr. Opin. Chem. Biol. 3:466–473).

PDE5 is highly selective for cGMP as a substrate (Turko, I. V. et al. (1998) Biochemistry 37:42004205), and has two allosteric cGMP-specific binding sites (McAllister-Lucas, L. M. et al. (1995) J. Biol. Chem. 270:30671–30679). Binding of cGMP to these allosteric binding sites seems to be important for phosphorylation of PDE5 by cGMP-dependent protein kinase rather than for direct regulation of catalytic activity. High levels of PDE5 are found in vascular smooth muscle, platelets, lung, and kidney. The inhibitor zaprinast is effective against PDE5 and PDE 1s. Modification of zaprinast to provide specificity against PDE5 has resulted in sildenafil (VIAGRA; Pfizer, Inc., New York N.Y.), a treatment for male erectile dysfunction (Terrett, N. et al. (1996) Bioorg. Med. Chem. Lett. 6:1819–1824). Inhibitors of PDE5 are currently being studied as agents for cardiovascular therapy (Perry, M. J. and G. A. Higgs (1998) Curr. Opin. Chem. Biol. 2:472–481).

PDE6s, the photoreceptor cyclic nucleotide phosphodiesterases, are crucial components of the phototransduction cascade. In association with the G-protein transducin, PDE6s hydrolyze cGMP to regulate cGMP-gated cation channels in photoreceptor membranes. In addition to the cGMP-binding active site, PDE6s also have two high-affinity cGMP-binding sites which are thought to play a regulatory role in PDE6 function (Artemyev, N. O. et al. (1998) Methods 14:93–104). Defects in PDE6s have been associated with retinal disease. Retinal degeneration in the rd mouse (Yan, W. et al. (1998) Invest. Opthalmol. Vis. Sci. 39:2529–2536), autosomal recessive retinitis pigmentosa in humans (Danciger, M. et al. (1995) Genomics 30:1–7), and rod/cone dysplasia 1 in Irish Setter dogs (Suber, M. L. et al. (1993) Proc. Natl. Acad. Sci. USA 90:3968–3972) have been attributed to mutations in the PDE6B gene.

The PDE7 family of PDEs consists of only one known member having multiple splice variants (Bloom, T. J. and J. A. Beavo (1996) Proc. Natl. Acad. Sci. USA 93:14188–14192). PDE7s are cAMP specific, but little else is known about their physiological function. Although mRNAs encoding PDE7s are found in skeletal muscle, heart, brain, lung, kidney, and pancreas, expression of PDE7 proteins is restricted to specific tissue types (Han, P. et al. (1997) J. Biol. Chem. 272:16152–16157; Perry, M. J. and G. A. Higgs (1998) Curr. Opin. Chem. Biol. 2:472–481). PDE7s are very closely related to the PDE4 family; however, PDE7s are not inhibited by rolipram, a specific inhibitor of PDE4s (Beavo, supra).

PDE8s are cAMP specific, and are closely related to the PDE4 family. PDE8s are expressed in thyroid gland, testis, eye, liver, skeletal muscle, heart, kidney, ovary, and brain. The cAMP-hydrolyzing activity of PDE8s is not inhibited by the PDE inhibitors rolipram, vinpocetine, milrinone, IBMX (3-isobutyl-1-methylxanthine), or zaprinast, but PDE8s are inhibited by dipyridamole (Fisher, D. A. et al. (1998) Biochem. Biophys. Res. Commun. 246:570–577; Hayashi, M. et al. (1998) Biochem. Biophys. Res. Commun. 250:751–756; Soderling, S. H. et al. (1998) Proc. Natl. Acad. Sci. USA 95:8991–8996).

PDE9s are cGMP specific and most closely resemble the PDE8 family of PDEs. PDE9s are expressed in kidney, liver, lung, brain, spleen, and small intestine. PDE9s are not inhibited by sildenafil (VIAGRA; Pfizer, Inc., New York N.Y.), rolipram, vinpocetine, dipyridamole, or IBMX (3-isobutyl-1-methylxanthine), but they are sensitive to the PDE5 inhibitor zaprinast (Fisher, D. A. et al. (1998) J. Biol. Chem. 273:15559–15564; Soderling, S. H. et al. (1998) J. Biol. Chem. 273:15553–15558).

PDE10s are dual-substrate PDEs, hydrolyzing both cAMP and cGMP. PDE10s are expressed in brain, thyroid, and testis. (Soderling, S. H. et al. (1999) Proc. Natl. Acad. Sci. USA 96:7071–7076; Fujishige, K. et al. (1999) J. Biol. Chem. 274:18438–18445; Loughney, K. et al (1999) Gene 234:109–117).

Cyclic Nucleotide Phosphodiesterase Structure

PDEs are composed of a catalytic domain of about 270–300 amino acids, an N-terminal regulatory domain responsible for binding cofactors, and, in some cases, a hydrophilic C-terminal domain of unknown function (Conti, M. and S.-L. C. Jin (1999) Prog. Nucleic Acid Res. Mol. Biol. 63:1–38). A conserved, putative zinc-binding motif has been identified in the catalytic domain of all PDEs. N-terminal regulatory domains include non-catalytic cGMP-binding domains in PDE2s, PDE5s, and PDE6s; calmodulin-binding domains in PDE1s; and domains containing phosphorylation sites in PDE3s and PDE4s. In PDE5, the N-terminal cGMP-binding domain spans about 380 amino acid residues and comprises tandem repeats of a conserved sequence motif (McAllister-Lucas, L. M. et al. (1993) J. Biol. Chem. 268:22863–22873). This motif has been shown by mutagenesis to be important for cGMP binding (Turko, I. V. et al. (1996) J. Biol. Chem. 271:22240–22244). PDE families display approximately 30% amino acid identity within the catalytic domain; however, isozymes within the same family typically display about 85–95% identity in this region (e.g. PDE4A vs PDE4B). Furthermore, within a family there is extensive similarity (>60%) outside the catalytic domain; while across families, there is little or no sequence similarity outside this domain.

Cyclic Nucleotide Phosphodiesterases in Disease

Many of the constituent functions of immune and inflammatory responses are inhibited by agents that increase intracellular levels of cAMP (Verghese, M. W. et al. (1995) Mol. Pharmacol. 47:1164–1171). A variety of diseases have been attributed to increased PDE activity and associated with decreased levels of cyclic nucleotides. For example, a form of diabetes insipidus in mice has been associated with increased PDE4 activity, an increase in low-$K_m$ cAMP PDE activity has been reported in leukocytes of atopic patients, and PDE3 has been associated with cardiac disease.

Many inhibitors of PDEs have been identified and have undergone clinical evaluation (Perry, M. J. and G. A. Higgs (1998) Curr. Opin. Chem. Biol. 2:472–481; Torphy, T. J. (1998) Am. J. Respir. Crit. Care Med. 157:351–370). PDE3 inhibitors are being developed as antithrombotic agents, antihypertensive agents, and as cardiotonic agents useful in the treatment of congestive heart failure. Rolipram, a PDE4 inhibitor, has been used in the treatment of depression, and other inhibitors of PDE4 are undergoing evaluation as anti-inflammatory agents. Rolipram has also been shown to inhibit lipopolysaccharide (LPS) induced TNF-α which has been shown to enhance HIV-1replication in vitro. Therefore, rolipram may inhibit HIV-1 replication (Angel, J. B. et al. (1995) AIDS 9:1137–1144). Additionally, rolipram, based on its ability to suppress the production of cytokines such as TNF-α and β and interferon γ, has been shown to be effective in the treatment of encephalomyelitis. Rolipram may also be effective in treating tardive dyskinesia and was effective in treating multiple sclerosis in an experimental animal model (Sommer, N. et al. (1995) Nat. Med. 1:244–248; Sasaki, H. et al. (1995) Eur. J. Pharmacol. 282:71–76).

Theophylline is a nonspecific PDE inhibitor used in the treatment of bronchial asthma and other respiratory diseases. Theophylline is believed to act on airway smooth muscle function and in an anti-inflammatory or immunomodulatory capacity in the treatment of respiratory diseases (Banner, K. H. and C. P. Page (1995) Eur. Respir. J. 8:996–1000). Pentoxifylline is another nonspecific PDE inhibitor used in the treatment of intermittent claudication and diabetes-induced peripheral vascular disease. Pentoxifylline is also known to block TNF-α production and may inhibit HIV1 replication (Angel et al., supra).

PDEs have been reported to affect cellular proliferation of a variety of cell types (Conti et al. (1995) Endocrine Rev. 16:370–389) and have been implicated in various cancers. Growth of prostate carcinoma cell lines DU145 and LNCaP was inhibited by delivery of cAMP derivatives and PDE inhibitors (Bang, Y. J. et al. (1994) Proc. Natl. Acad. Sci. USA 91:5330–5334). These cells also showed a permanent conversion in phenotype from epithelial to neuronal morphology. It has also been suggested that PDE inhibitors have the potential to regulate mesangial cell proliferation (Matousovic, K. et al. (1995) J. Clin. Invest. 96:401–410) and lymphocyte proliferation (Joulain, C. et al. (1995) J. Lipid Mediat. Cell Signal. 11:63–79). A cancer treatment has been described that involves intracellular delivery of PDEs to particular cellular compartments of tumors, resulting in cell death (Deonarain, M. P. and A. A. Epenetos (1994) Br. J. Cancer 70:786–794).

The discovery of new phosphodiesterases and the polynucleotides encoding them satisfies a need in the art by providing new compositions which are useful in the diagnosis, prevention, and treatment of eye, neurological, cardiovascular, cell proliferative, and autoimmune/inflammatory disorders, and in the assessment of the effects of exogenous compounds on the expression of nucleic acid and amino acid sequences of phosphodiesterases.

SUMMARY OF THE INVENTION

The invention features purified polypeptides, phosphodiesterases, referred to collectively as "HPDE" and individually as "HPDE-1," "HPDE-2," and "HPDE-3." In one aspect, the invention provides an isolated polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. In one alternative, the invention provides an isolated polypeptide comprising the amino acid sequence of SEQ ID NO:1–3.

The invention further provides an isolated polynucleotide encoding a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. In one alternative, the polynucleotide encodes a polypeptide selected from the group consisting of SEQ ID NO:1–3. In another alternative, the polynucleotide is selected from the group consisting of SEQ ID NO:4–6.

Additionally, the invention provides a recombinant polynucleotide comprising a promoter sequence operably linked to a polynucleotide encoding a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. In one alternative, the invention provides a cell transformed with the recombinant polynucleotide. In another alternative, the invention provides a transgenic organism comprising the recombinant polynucleotide.

The invention also provides a method for producing a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3.

The invention further provides an isolated polynucleotide comprising a polynucleotide sequence selected from the group consisting of a) a polynucleotide sequence selected from the group consisting of SEQ ID NO:4–6, b) a naturally occurring polynucleotide sequence having at least 90% sequence identity to a polynucleotide sequence selected from the group consisting of SEQ ID NO:4–6, c) a polynucleotide sequence complementary to a), d) a polynucleotide sequence complementary to b), and e) an RNA equivalent of a)–d). In one alternative, the polynucleotide comprises at least 60 contiguous nucleotides.

Additionally, the invention provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:4–6, b) a naturally occurring polynucleotide sequence having at least 90% sequence identity to a polynucleotide sequence selected from the group consisting of SEQ ID NO:4–6, c) a polynucleotide sequence complementary to a), d) a polynucleotide sequence complementary to b), and e) an RNA equivalent of a)–d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:4–6, b) a naturally occurring polynucleotide sequence having at least 90% sequence identity to a polynucleotide sequence selected from the group consisting of SEQ ID NO:4–6, c) a polynucleotide sequence complementary to a), d) a polynucleotide sequence complementary to b), and e) an RNA equivalent of a)–d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3, and a pharmaceutically acceptable excipient. In one embodiment, the composition comprises an amino acid sequence selected from the group consisting of SEQ ID NO:1–3. The invention additionally provides a method of treating a disease or condition associated with decreased expression of functional HPDE, comprising administering to a patient in need of such treatment the composition.

The invention also provides a method for screening a compound for effectiveness as an agonist of a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional HPDE, comprising administering to a patient in need of such treatment the composition.

Additionally, the invention provides a method for screening a compound for effectiveness as an antagonist of a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional HPDE, comprising administering to a patient in need of such treatment the composition.

The invention further provides a method of screening for a compound that specifically binds to a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide comprising an amino acid sequence selected from the group consisting of a) an amino acid sequence selected from the group consisting of SEQ ID NO:1–3, b) a naturally occurring amino acid sequence having at least 90% sequence identity to an amino acid sequence selected from the group consisting of SEQ ID NO:1–3, c) a biologically active fragment of an amino acid sequence selected from the group consisting of SEQ ID NO:1–3, and d) an immunogenic fragment of an amino acid sequence selected from the group consisting of SEQ ID NO:1–3. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a sequence selected from the group consisting of SEQ ID NO:4–6, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide comprising a polynucleotide sequence selected from the group consisting of i) a polynucleotide sequence selected from the group consisting of SEQ ID NO:4–6, ii) a naturally occurring polynucleotide sequence having at least 90% sequence identity to a polynucleotide sequence selected from the group consisting of SEQ ID NO:4–6, iii) a polynucleotide sequence complementary to i), iv) a polynucleotide sequence complementary to ii), and v) an RNA equivalent of i)–iv). Hybridization occurs under conditions whereby a specific hybridization complex is formed between said probe and a target polynucleotide in the biological sample, said target polynucleotide comprising a polynucleotide sequence selected from the group consisting of i) a polynucleotide sequence selected from the group consisting of SEQ ID NO:4–6, ii) a naturally occurring polynucleotide sequence having at least 90% sequence identity to a polynucleotide sequence selected from the group consisting of SEQ ID NO:4–6, iii) a polynucleotide sequence complementary to i), iv) a polynucleotide sequence complementary to ii), and v) an RNA equivalent of i)–iv). Alternatively, the target polynucleotide comprises a fragment of a polynucleotide sequence selected from the group consisting of i)–v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE TABLES

Table 1 summarizes the nomenclature for the full length polynucleotide and polypeptide sequences of the present invention.

Table 2 shows the GenBank identification number and annotation of the nearest GenBank homolog for polypeptides of the invention. The probability score for the match between each polypeptide and its GenBank homolog is also shown.

Table 3 shows structural features of polypeptide sequences of the invention, including predicted motifs and domains, along with the methods, algorithms, and searchable databases used for analysis of the polypeptides.

Table 4 lists the cDNA fragments which were used to assemble polynucleotide sequences of the invention, along with selected fragments of the polynucleotide sequences.

Table 5 shows the representative cDNA library for polynucleotides of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"HPDE" refers to the amino acid sequences of substantially purified HPDE obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of HPDE. Agonists may include proteins, nucleic acids, carbohydrates, small molecules, or any other compound or composition which modulates the activity of HPDE either by directly interacting with HPDE or by acting on components of the biological pathway in which HPDE participates.

An "allelic variant" is an alternative form of the gene encoding HPDE. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HPDE include those sequences with deletions, insertions, or substitutions of different nucleotides, resulting in a polypeptide the same as HPDE or a polypeptide with at least one functional characteristic of HPDE. Included within this definition are polymorphisms which may or may not be readily detectable using a particular oligonucleotide probe of the polynucleotide encoding HPDE, and improper or unexpected hybridization to allelic variants, with a locus other than the normal chromosomal locus for the polynucleotide sequence encoding HPDE. The encoded protein may also be "altered," and may contain deletions, insertions, or substitutions of amino acid residues which produce a silent change and result in a functionally equivalent HPDE. Deliberate amino acid substitutions may be made on the basis of similarity in polarity, charge, solubility, hydrophobicity, hydrophilicity, and/or the amphipathic nature of the residues, as long as the biological or immunological activity of HPDE is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of HPDE. Antagonists may include proteins such as antibodies, nucleic acids, carbohydrates, small molecules, or any other compound or composition which modulates the activity of HPDE either by directly interacting with HPDE or by acting on components of the biological pathway in which HPDE participates.

The term "antibody" refers to intact immunoglobulin molecules as well as to fragments thereof, such as Fab, F(ab')$_2$, and Fv fragments, which are capable of binding an epitopic determinant. Antibodies that bind HPDE polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic HPDE, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding HPDE or fragments of HPDE may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |

-continued

| Original Residue | Conservative Substitution |
|---|---|
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe,Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

A "fragment" is a unique portion of HPDE or the polynucleotide encoding HPDE which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:4–6 comprises a region of unique polynucleotide sequence that specifically identifies SEQ ID NO:4–6, for example, as distinct from any other sequence in the genome from which the fragment was obtained. A fragment of SEQ ID NO:4–6 is useful, for example, in hybridization and amplification technologies and in analogous methods that distinguish SEQ ID NO:4–6 from related polynucleotide sequences. The precise length of a fragment of SEQ ID NO:4–6 and the region of SEQ ID NO:4–6 to which the fragment corresponds are routinely determinable by one of ordinary skill in the art based on the intended purpose for the fragment.

A fragment of SEQ ID NO:1–3 is encoded by a fragment of SEQ ID NO:4–6. A fragment of SEQ ID NO:1–3 comprises a region of unique amino acid sequence that specifically identifies SEQ ID NO:1–3. For example, a fragment of SEQ ID NO:1–3 is useful as an immunogenic peptide for the development of antibodies that specifically recognize SEQ ID NO:1–3. The precise length of a fragment of SEQ ID NO:1–3 and the region of SEQ ID NO:1–3 to which the fragment corresponds are routinely determinable by one of ordinary skill in the art based on the intended purpose for the fragment.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151–153 and in Higgins, D. G. et al. (1992) CABIOS 8:189–191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403–410), which is available from several sources, including the NCBI, Bethesda, Md., and on the Internet at http://www.ncbi.nlm.nih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/b12.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr.21 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: II and Extension Gap: 1 penalties
Gap x drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 μg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, 2$^{nd}$ ed., vol. 1–3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100–200 μg/ml. Organic solvent, such as formamide at a concentration of about 35–50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of HPDE which is capable of eliciting an immune response when introduced into a living organism, for example, a mammal. The term "immunogenic fragment" also includes any polypeptide or oligopeptide fragment of HPDE which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of HPDE. For example, modulation may cause an increase or a decrease in protein activity, binding characteristics, or any other biological, functional, or immunological properties of HPDE.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an HPDE may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of HPDE.

"Probe" refers to nucleic acid sequences encoding HPDE, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual*, $2^{nd}$ ed., vol. 1–3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing HPDE, nucleic acids encoding HPDE, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 07, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternative splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 07. 1999) set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The Invention

The invention is based on the discovery of new human phosphodiesterases (HPDE), the polynucleotides encoding HPDE, and the use of these compositions for the diagnosis, treatment, or prevention of eye, neurological, cardiovascular, cell proliferative, and autoimmune/inflammatory disorders.

Table 1 summarizes the nomenclature for the full length polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (Genbank ID NO:) of the nearest GenBank homolog. Column 4 shows the probability score for the match between each polypeptide and its GenBank homolog. Column 5 shows the annotation of the GenBank homolog.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are phosphodiesterases. For example, SEQ ID NO:1 is 34% identical to human phosphodiesterase I/nucleotide pyrophosphatase 1 PC1/NPPS (GenBank ID g9453796) as determined by the Basic Local Alignment Search Tool (BLAST). (See Table 2.) The BLAST probability score is 3.00e-63, which indicates the probability of obtaining the observed polypeptide sequence alignment by chance. SEQ ID NO:1 also contains a type I phosphodiesterase domain as determined by searching for statistically significant matches in the hidden Markov model (HMM)-based PFAM database of conserved protein family domains. (See Table 3.) Data from BLAST analyses provide further corroborative evidence that SEQ ID NO:1 is a phosphodiesterase. SEQ ID NO:2 and SEQ ID NO:3 were analyzed and annotated in a similar manner. The algorithms and parameters for the analysis of SEQ ID NO:1–3 are described in Table 7.

As shown in Table 4, the full length polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:4–6 or that distinguish between SEQ ID NO:4–6 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the full length polynucleotide sequences of the invention. Columns 6 and 7 of Table 4 show the nucleotide start (5') and stop (3') positions of the cDNA sequences in column 5 relative to their respective full length sequences.

The identification numbers in Column 5 of Table 4 may refer specifically, for example, to Incyte cDNAs along with their corresponding cDNA libraries. For example, 6777323H1 is the identification number of an Incyte cDNA sequence, and OVARDIR01 is the cDNA library from which it is derived. Incyte cDNAs for which cDNA libraries are not indicated were derived from pooled cDNA libraries (e.g., 70695293V1). Alternatively, the identification numbers in column 5 may refer to GenBank cDNAs or ESTs which contributed to the assembly of the full length polynucleotide sequences. Alternatively, the identification numbers in column 5 may refer to coding regions predicted by Genscan analysis of genomic DNA. The Genscan-predicted coding sequences may have been edited prior to assembly. (See Example IV.) Alternatively, the identification numbers in column 5 may refer to assemblages of both cDNA and Genscan-predicted exons brought together by an "exon stitching" algorithm. (See Example V.) Alternatively, the identification numbers in column 5 may refer to assemblages of both cDNA and Genscan-predicted exons brought together by an "exon-stretching" algorithm. (See Example V.) In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those full length polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses HPDE variants. A preferred HPDE variant is one which has at least about 80%, or alternatively at least about 90%, or even at least about 95% amino acid sequence identity to the HPDE amino acid sequence, and which contains at least one functional or structural characteristic of HPDE.

The invention also encompasses polynucleotides which encode HPDE. In a particular embodiment, the invention encompasses a polynucleotide sequence comprising a sequence selected from the group consisting of SEQ ID NO:4–6, which encodes HPDE. The polynucleotide sequences of SEQ ID NO:4–6, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding HPDE. In particular, such a variant polynucleotide sequence will have at least about 70%, or alternatively at least about 85%, or even at least about 95% polynucleotide sequence identity to the polynucleotide sequence encoding HPDE. A particular aspect of the invention encompasses a variant of a polynucleotide sequence comprising a sequence selected from the group consisting of SEQ ID NO:4–6 which has at least about 70%, or alternatively at least about 85%, or even at least about 95% polynucleotide sequence identity to a nucleic acid sequence selected from the group consisting of SEQ ID NO:4–6. Any one of the polynucleotide variants described above can encode an amino acid sequence which contains at least one functional or structural characteristic of HPDE.

It will be appreciated by those skilled in the art that as a result of the degeneracy of the genetic code, a multitude of polynucleotide sequences encoding HPDE, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HPDE, and all such variations are to be considered as being specifically disclosed.

Although nucleotide sequences which encode HPDE and its variants are generally capable of hybridizing to the nucleotide sequence of the naturally occurring HPDE under appropriately selected conditions of stringency, it may be advantageous to produce nucleotide sequences encoding HPDE or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HPDE and its derivatives without altering the encoded amino acid sequences include the production of RNA transcripts having more desirable properties, such as a greater half-life, than transcripts produced from the naturally occurring sequence.

The invention also encompasses production of DNA sequences which encode HPDE and HPDE derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HPDE or any fragment thereof.

Also encompassed by the invention are polynucleotide sequences that are capable of hybridizing to the claimed polynucleotide sequences, and, in particular, to those shown in SEQ ID NO:4–6 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding HPDE may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HPDE may be cloned in recombinant DNA molecules that direct expression of HPDE, or fragments or functional equivalents thereof, in appropriate host cells. Due to the inherent degeneracy of the genetic code, other DNA sequences which encode substantially the same or a functionally equivalent amino acid sequence may be produced and used to express HPDE.

The nucleotide sequences of the present invention can be engineered using methods generally known in the art in order to alter HPDE-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULARBREEDING (Maxygen Inc., Santa Clara Calif.; described in U.S. Pat. No. 5,837,458; Chang, C.-C. et al. (1999) Nat. Biotechnol. 17:793–797; Christians, F. C. et al. (1999) Nat. Biotechnol. 17:259–264; and Crameri, A. et al. (1996) Nat. Biotechnol. 14:315–319) to alter or improve the biological properties of HPDE, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding HPDE may be synthesized, in whole or in part, using chemical methods well known in the art. (See, e.g., Caruthers, M. H. et al. (1980) Nucleic Acids Symp. Ser. 7:215–223; and Horn, T. et al. (1980) Nucleic Acids Symp. Ser. 7:225–232.) Alternatively, HPDE itself or a fragment thereof may be synthesized using chemical methods. For example, peptide synthesis can be performed using various solution-phase or solid-phase techniques. (See, e.g., Creighton, T. (1984) *Proteins. Structures and Molecular Properties,* W H Freeman, New York N.Y., pp.55–60; and Roberge, J. Y. et al. (1995) Science 269:202–204.) Automated synthesis may be achieved using the ABI 431A peptide synthesizer (Applied Biosystems). Additionally, the amino acid sequence of HPDE, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392–421.) The composition of the synthetic peptides may be confirmed by amino acid analysis or by sequencing. (See, e.g., Creighton, supra, pp. 28–53.)

In order to express a biologically active HPDE, the nucleotide sequences encoding HPDE or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HPDE. Such elements may vary in their strength and specificity. Specific initiation signals may also be used to achieve more efficient translation of sequences encoding HPDE. Such signals include the ATG initiation codon and adjacent sequences, e.g. the Kozak sequence. In cases where sequences encoding HPDE and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding HPDE and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding HPDE. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503–5509; Engelhard, E. K. et al. (1994) Proc. Natl. Acad. Sci. USA 91:3224–3227; Sandig, V. et al. (1996) Hum. Gene Ther. 7:1937–1945; Takamatsu, N. (1987) EMBO J. 6:307–311; *The McGraw Hill Yearbook of Science and Technology* (1992) McGraw Hill, New York N.Y., pp. 191–196; Logan, J. and T. Shenk (1984) Proc. Natl. Acad. Sci. USA 81:3655–3659; and Harrington, J. J. et al. (1997) Nat. Genet. 15:345–355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther. 5(6):350–356; Yu, M. et al. (1993) Proc. Natl. Acad. Sci. USA 90(13):6340–6344; Buller, R. M. et al. (1985) Nature 317(6040):813–815; McGregor, D. P. et al. (1994) Mol. Immunol. 31(3):219–226; and Verma, I. M. and N. Somia (1997) Nature 389:239–242.) The invention is not limited by the host cell employed.

In bacterial systems, a number of cloning and expression vectors may be selected depending upon the use intended for polynucleotide sequences encoding HPDE. For example, routine cloning, subcloning, and propagation of polynucleotide sequences encoding HPDE can be achieved using a multifunctional *E. coli* vector such as PBLUESCRIPT (Stratagene, La Jolla Calif.) or PSPORT1 plasmid (Life Technologies). Ligation of sequences encoding HPDE into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of HPDE are needed, e.g. for the production of antibodies, vectors which direct high level expression of HPDE may be used. For example, vectors containing the strong, inducible SP6 or T7 bacteriophage promoter may be used.

Yeast expression systems may be used for production of HPDE. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516–544; and Scorer, C. A. et al. (1994) Bio/Technology 12:181–184.)

Plant systems may also be used for expression of HPDE. Transcription of sequences encoding HPDE may be driven by viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding HPDE may be ligated into an adenovirus transcription/translation complex consisting of the late promoter and tripartite leader sequence. Insertion in a non-essential E1 or E3 region of the viral genome may be used to obtain infective virus which expresses HPDE in host cells. (See, e.g., Logan, J. and T. Shenk (1984) Proc. Natl. Acad. Sci. USA 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345–355.)

For long term production of recombinant proteins in mammalian systems, stable expression of HPDE in cell lines is preferred. For example, sequences encoding HPDE can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ and apr⁻ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively. (See, e.g., Wigler, M. et al. (1980) Proc. Natl. Acad. Sci. USA 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding HPDE is inserted within a marker gene sequence, transformed cells containing sequences encoding HPDE can be identified by the absence of marker gene function. Alternatively, a marker gene can be placed in tandem with a sequence encoding HPDE under the control of a single promoter. Expression of the marker gene in response to induction or selection usually indicates expression of the tandem gene as well.

In general, host cells that contain the nucleic acid sequence encoding HPDE and that express HPDE may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HPDE using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HPDE is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino acid assays. Means for producing labeled hybridization or PCR probes for detecting sequences related to polynucleotides encoding HPDE include oligolabeling, nick translation, end-labeling, or PCR amplification using a labeled nucleotide. Alternatively, the sequences encoding HPDE, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HPDE may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HPDE may be designed to contain signal sequences which direct secretion of HPDE through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant nucleic acid sequences encoding HPDE may be ligated to a heterologous sequence resulting in translation of a fusion protein in any of the aforementioned host systems. For example, a chimeric HPDE protein containing a heterologous moiety that can be recognized by a commercially available antibody may facilitate the screening of peptide libraries for inhibitors of HPDE activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HPDE encoding sequence and the heterologous protein sequence, so that HPDE may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled HPDE may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

HPDE of the present invention or fragments thereof may be used to screen for compounds that specifically bind to HPDE. At least one and up to a plurality of test compounds may be screened for specific binding to HPDE. Examples of test compounds include antibodies, oligonucleotides, proteins (e.g., receptors), or small molecules.

In one embodiment, the compound thus identified is closely related to the natural ligand of HPDE, e.g., a ligand or fragment thereof, a natural substrate, a structural or functional mimetic, or a natural binding partner. (See, e.g., Coligan, J. E. et al. (1991) Current Protocols in Immunology 1(2): Chapter 5.) Similarly, the compound can be closely related to the natural receptor to which HPDE binds, or to at least a fragment of the receptor, e.g., the ligand binding site. In either case, the compound can be rationally designed using known techniques. In one embodiment, screening for these compounds involves producing appropriate cells which express HPDE, either as a secreted protein or on the cell membrane. Preferred cells include cells from mammals, yeast, Drosophila, or E. coli. Cells expressing HPDE or cell membrane fractions which contain HPDE are then contacted with a test compound and binding, stimulation, or inhibition of activity of either HPDE or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with HPDE, either in solution or affixed to a solid support, and detecting the binding of HPDE to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

HPDE of the present invention or fragments thereof may be used to screen for compounds that modulate the activity of HPDE. Such compounds may include agonists, antagonists, or partial or inverse agonists. In one embodiment, an assay is performed under conditions permissive for HPDE activity, wherein HPDE is combined with at least one test compound, and the activity of HPDE in the presence of a test compound is compared with the activity of HPDE in the absence of the test compound. A change in the activity of HPDE in the presence of the test compound is indicative of a compound that modulates the activity of HPDE. Alternatively, a test compound is combined with an in vitro or cell-free system comprising HPDE under conditions suitable for HPDE activity, and the assay is performed. In either of these assays, a test compound which modulates the activity of HPDE may do so indirectly and need not come in direct contact with the test compound. At least one and up to a plurality of test compounds may be screened.

In another embodiment, polynucleotides encoding HPDE or their mammalian homologs may be "knocked out" in an animal model system using homologous recombination in embryonic stem (ES) cells. Such techniques are well known in the art and are useful for the generation of animal models of human disease. (See, e.g., U.S. Pat. Nos. 5,175,383 and 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288–1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999–2002; Wagner, K. U. et al. (1997) Nucleic Acids Res. 25:4323–4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding HPDE may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282:1145–1147).

Polynucleotides encoding HPDE can also be used to create "knockin" humanized animals (pigs) or transgenic animals (mice or rats) to model human disease. With knockin technology, a region of a polynucleotide encoding HPDE is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress HPDE, e.g., by secreting HPDE in its milk, may also serve as a convenient source of that protein (Janne, J. et al. (1998) Biotechnol. Annu. Rev. 4:55–74).

Therapeutics

Chemical and structural similarity, e.g., in the context of sequences and motifs, exists between regions of HPDE and phosphodiesterases. Therefore, HPDE appears to play a role in eye, neurological, cardiovascular, cell proliferative, and autoimmune/inflammatory disorders. In the treatment of disorders associated with increased HPDE expression or activity, it is desirable to decrease the expression or activity of HPDE. In the treatment of disorders associated with decreased HPDE expression or activity, it is desirable to increase the expression or activity of HPDE.

Therefore, in one embodiment, HPDE or a fragment or derivative thereof may be administered to a subject to treat or prevent a disorder associated with decreased expression or activity of HPDE. Examples of such disorders include, but are not limited to, an eye disorder, such as conjunctivitis, keratoconjunctivitis sicca, keratitis, episcleritis, iritis, posterior uveitis, glaucoma, amaurosis fugax, ischemic optic neuropathy, optic neuritis, Leber's hereditary optic neuropathy, toxic optic neuropathy, vitreous detachment, retinal detachment, cataract, macular degeneration, central serous chorioretinopathy, retinitis pigmentosa, melanoma of the choroid, retrobulbar tumor, and chiasmal tumor; a neurological disorder, such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a cardiovascular disorder, such as arterioyenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; a cell proliferative disorder, such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an autoimmune/inflammatory disorder, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing HPDE or a fragment or derivative thereof may be administered to a subject to treat or prevent a disorder associated with decreased expression or activity of HPDE including, but not limited to, those described above.

In a further embodiment, a composition comprising a substantially purified HPDE in conjunction with a suitable pharmaceutical carrier may be administered to a subject to treat or prevent a disorder associated with decreased expression or activity of HPDE including, but not limited to, those provided above.

In still another embodiment, an agonist which modulates the activity of HPDE may be administered to a subject to treat or prevent a disorder associated with decreased expression or activity of HPDE including, but not limited to, those listed above.

In a further embodiment, an antagonist of HPDE may be administered to a subject to treat or prevent a disorder associated with increased expression or activity of HPDE. Examples of such disorders include, but are not limited to, those eye, neurological, cardiovascular, cell proliferative, and autoimmune/inflammatory disorders described above. In one aspect, an antibody which specifically binds HPDE may be used directly as an antagonist or indirectly as a targeting or delivery mechanism for bringing a pharmaceutical agent to cells or tissues which express HPDE.

In an additional embodiment, a vector expressing the complement of the polynucleotide encoding HPDE may be administered to a subject to treat or prevent a disorder associated with increased expression or activity of HPDE including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HPDE may be produced using methods which are generally known in the art. In particular, purified HPDE may be used to produce antibodies or to screen libraries of pharmaceutical agents to identify those which specifically bind HPDE. Antibodies to HPDE may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with HPDE or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HPDE have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of HPDE amino acids may be fused with those of another protein, such as KLH, and antibodies to the chimeric molecule may be produced.

Monoclonal antibodies to HPDE may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. USA 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. USA 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HPDE-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833–3837; Winter, G. et al. (1991) Nature 349:293–299.)

Antibody fragments which contain specific binding sites for HPDE may also be generated. For example, such fragments include, but are not limited to, F(ab')$_2$ fragments produced by pepsin digestion of the antibody molecule and Fab fragments generated by reducing the disulfide bridges of the F(ab')$_2$ fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HPDE and its specific antibody. A two-site, monoclonal-based immunoassay utilizing monoclonal antibodies reactive to two non-interfering HPDE epitopes is generally used, but a competitive binding assay may also be employed (Pound, supra).

Various methods such as Scatchard analysis in conjunction with radioimmunoassay techniques may be used to assess the affinity of antibodies for HPDE. Affinity is expressed as an association constant, $K_a$, which is defined as the molar concentration of HPDE-antibody complex divided by the molar concentrations of free antigen and free antibody under equilibrium conditions. The $K_a$ determined for a preparation of polyclonal antibodies, which are heterogeneous in their affinities for multiple HPDE epitopes, represents the average affinity, or avidity, of the antibodies for HPDE. The $K_a$ determined for a preparation of monoclonal antibodies, which are monospecific for a particular HPDE epitope, represents a true measure of affinity. High-affinity antibody preparations with $K_a$ ranging from about $10^9$ to $10^{12}$ L/mole are preferred for use in immunoassays in which the HPDE-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HPDE, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is generally employed in procedures requiring precipitation of HPDE-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HPDE, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding HPDE. Such technology is well known in the art, and antisense oligonucleotides or larger fragments can be designed from various locations along the coding or control regions of sequences encoding HPDE. (See, e.g., Agrawal, S., ed. (1996) *Antisense Therapeutics*, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al. (1998) J. Allergy Cli. Immunol. 102(3):469–475; and Scanlon, K. J. et al. (1995) 9(13):1288–1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323–347.) Other gene delivery mechanisms include liposome-derived systems, artificial viral envelopes, and other systems known in the art. (See, e.g., Rossi, J. J. (1995) Br. Med. Bull. 51(1):217–225; Boado, R. J. et al. (1998) J. Pharm. Sci. 87(11):1308–1315; and Morris, M. C. et al. (1997) Nucleic Acids Res. 25(14):2730–2736.)

In another embodiment of the invention, polynucleotides encoding HPDE may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669–672), severe combined immunodeficiency syndrome associated with an inherited adenosine deaminase (ADA) deficiency (Blaese, R. M. et al. (1995) Science 270:475–480; Bordignon, C. et al. (1995) Science 270:470–475), cystic fibrosis (Zabner, J. et al. (1993) Cell 75:207–216; Crystal, R. G. et al. (1995) Hum. Gene Therapy 6:643–666; Crystal, R. G. et al. (1995) Hum. Gene Therapy 6:667–703), thalassamias, familial hypercholesterolemia, and hemophilia resulting from Factor VIII or Factor IX deficiencies (Crystal, R. G. (1995) Science 270:404–410; Verma, I. M. and N. Somia (1997) Nature 389:239–242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:395–396; Poeschla, E. et al. (1996) Proc. Natl. Acad. Sci. USA. 93:11395–11399), hepatitis B or C virus (HBV, HCV); fungal parasites, such as *Candida albicans* and *Paracoccidioides brasiliensis;* and protozoan parasites such as *Plasmodium falciparum* and *Trypanosoma cruzi*). In the case where a genetic deficiency in HPDE expression or regulation causes disease, the expression of HPDE from an appropriate population of transduced cells may alleviate the clinical manifestations caused by the genetic deficiency.

In a further embodiment of the invention, diseases or disorders caused by deficiencies in HPDE are treated by constructing mammalian expression vectors encoding HPDE and introducing these vectors by mechanical means into HPDE-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191–217; Ivics, Z. (1997) Cell 91:501–510; Boulay, J-L. and H. Récipon (1998) Curr. Opin. Biotechnol. 9:445–450).

Expression vectors that may be effective for the expression of HPDE include, but are not limited to, the PCDNA 3.1, EPITAG, PRCCMV2, PREP, PVAX vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). HPDE may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547–5551; Gossen, M. et al. (1995) Science 268:1766–1769; Rossi, F. M. V. and H. M. Blau (1998) Curr. Opin. Biotechnol. 9:451–456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and Blau, H. M. supra)), or (iii) a tissue-specific promoter or the native promoter of the endogenous gene encoding HPDE from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456–467), or by electroporation (Neumann, E. et al. (1982) EMBO J. 1:841–845). The introduction of DNA to primary cells requires modification of these standardized mammalian transfection protocols.

In another embodiment of the invention, diseases or disorders caused by genetic defects with respect to HPDE expression are treated by constructing a retrovirus vector consisting of (i) the polynucleotide encoding HPDE under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. USA 92:6733–6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647–1650; Bender, M. A. et al. (1987) J. Virol. 61:1639–1646; Adam, M. A. and A. D. Miller (1988) J. Virol. 62:3802–3806; Dull, T. et al. (1998) J. Virol. 72:8463–8471; Zufferey, R. et al. (1998) J. Virol. 72:9873–9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4$^+$ T-cells), and the return of transduced cells to a patient are procedures well known to persons skilled in the art of gene therapy and have been well documented (Ranga, U. et al. (1997) J. Virol. 71:7020–7029; Bauer, G. et al. (1997) Blood 89:2259–2267; Bonyhadi, M. L. (1997) J. Virol. 71:4707–4716; Ranga, U. et al. (1998) Proc. Natl. Acad. Sci. USA 95:1201–1206; Su, L. (1997) Blood 89:2283–2290).

In the alternative, an adenovirus-based gene therapy delivery system is used to deliver polynucleotides encoding HPDE to cells which have one or more genetic abnormalities with respect to the expression of HPDE. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263–268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511–544 and Verma, I. M. and N. Somia (1997) Nature 18:389:239–242, both incorporated by reference herein.

In another alternative, a herpes-based, gene therapy delivery system is used to deliver polynucleotides encoding HPDE to target cells which have one or more genetic abnormalities with respect to the expression of HPDE. The use of herpes simplex virus (HSV)-based vectors may be especially valuable for introducing HPDE to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385–395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519–532 and Xu, H. et al. (1994) Dev. Biol. 163:152–161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding HPDE to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464–469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for HPDE into the alphavirus genome in place of the capsid-coding region results in the production of a large number of HPDE-coding RNAs and the synthesis of high levels of HPDE in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74–83). The wide host range of alphaviruses will allow the introduction of HPDE into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HPDE.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HPDE. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding HPDE. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased HPDE expression or activity, a compound which specifically inhibits expression of the polynucleotide encoding HPDE may be therapeutically useful, and in the treament of disorders associated with decreased HPDE expression or activity, a compound which specifically promotes expression of the polynucleotide encoding HPDE may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding HPDE is exposed to at least one test compound thus obtained. The sample may comprise, for example, an intact or permeabilized cell, or an in vitro cell-free or reconstituted biochemical system. Alterations in the expression of a polynucleotide encoding HPDE are assayed by any method commonly known in the art. Typically, the expression of a specific nucleotide is detected by hybridization with a probe having a nucleotide sequence complementary to the sequence of the polynucleotide encoding HPDE. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomvces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8–13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462–466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of HPDE, antibodies to HPDE, and mimetics, agonists, antagonists, or inhibitors of HPDE.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising HPDE or fragments thereof. For example, liposome preparations containing a cell-impermeable macromolecule may promote cell fusion and intracellular delivery of the macromolecule. Alternatively, HPDE or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569–1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example HPDE or fragments thereof, antibodies of HPDE, and agonists, antagonists or inhibitors of HPDE, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HPDE may be used for the diagnosis of disorders characterized by expression of HPDE, or in assays to monitor patients being treated with HPDE or agonists, antagonists, or inhibitors of HPDE. Antibodies useful for diagnostic purposes may be prepared in the same manner as described above for therapeutics. Diagnostic assays for HPDE include methods which utilize the antibody and a label to detect HPDE in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HPDE, including ELISAs, RIAs, and FACS, are known in the art and provide a basis for diagnosing altered or abnormal levels of HPDE expression. Normal or standard values for HPDE expression are established by combining body fluids or cell extracts taken from normal mammalian subjects, for example, human subjects, with antibodies to HPDE under conditions suitable for complex formation. The amount of standard complex formation may be quantitated by various methods, such as photometric means. Quantities of HPDE expressed in subject, control, and disease samples from biopsied tissues are compared with the standard values. Deviation between standard and subject values establishes the parameters for diagnosing disease.

In another embodiment of the invention, the polynucleotides encoding HPDE may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of HPDE may be correlated with disease. The diagnostic assay may be used to determine absence, presence, and excess expression of HPDE, and to monitor regulation of HPDE levels during therapeutic intervention.

In one aspect, hybridization with PCR probes which are capable of detecting polynucleotide sequences, including genomic sequences, encoding HPDE or closely related molecules may be used to identify nucleic acid sequences which encode HPDE. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding HPDE, allelic variants, or related sequences.

Probes may also be used for the detection of related sequences, and may have at least 50% sequence identity to any of the HPDE encoding sequences. The hybridization probes of the subject invention may be DNA or RNA and may be derived from the sequence of SEQ ID NO:4–6 or from genomic sequences including promoters, enhancers, and introns of the HPDE gene.

Means for producing specific hybridization probes for DNAs encoding HPDE include the cloning of polynucleotide sequences encoding HPDE or HPDE derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HPDE may be used for the diagnosis of disorders associated with expression of HPDE. Examples of such disorders include, but are not limited to, an eye disorder, such as conjunctivitis, keratoconjunctivitis sicca, keratitis, episcleritis, iritis, posterior uveitis, glaucoma, amaurosis fugax, ischemic optic neuropathy, optic neuritis, Leber's hereditary optic neuropathy, toxic optic neuropathy, vitreous detachment, retinal detachment, cataract, macular degeneration, central serous chorioretinopathy, retinitis pigmentosa, melanoma of the choroid, retrobulbar tumor, and chiasmal tumor; a neurological disorder, such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system including Down syndrome, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a cardiovascular disorder, such as arterioyenous fistula, atherosclerosis, hypertension, vasculitis, Raynaud's disease, aneurysms, arterial dissections, varicose veins, thrombophlebitis and phlebothrombosis, vascular tumors, and complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation, congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, pleural tumors, drug-induced lung disease, radiation-induced lung disease, and complications of lung transplantation; a cell proliferative disorder, such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an autoimmune/inflammatory disorder, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding HPDE may be used in Southern or northern analysis, dot blot, or other membrane-based technologies; in PCR technologies; in dipstick, pin, and multiformat ELISA-like assays; and in microarrays utilizing fluids or tissues from patients to detect altered HPDE expression. Such qualitative or quantitative methods are well known in the art.

In a particular aspect, the nucleotide sequences encoding HPDE may be useful in assays that detect the presence of associated disorders, particularly those mentioned above. The nucleotide sequences encoding HPDE may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to control sample then the presence of altered levels of nucleotide sequences encoding HPDE in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HPDE, a normal or standard profile for expression is established. This may be accomplished by combining body fluids or cell extracts taken from normal subjects, either animal or human, with a sequence, or a fragment thereof, encoding HPDE, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HPDE may involve the use of PCR. These oligomers may be chemically synthesized, generated enzymatically, or produced in vitro. Oligomers will preferably contain a fragment of a polynucleotide encoding HPDE, or a fragment of a polynucleotide complementary to the polynucleotide encoding HPDE, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding HPDE may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding HPDE are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of HPDE include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212:229–236.) The speed of quantitation of multiple samples may be accelerated by running the assay in a high-throughput format where the oligomer or polynucleotide of interest is presented in various dilutions and a spectrophotometric or colorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, HPDE, fragments of HPDE, or antibodies specific for HPDE may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153–159; Steiner, S. and N. L. Anderson (2000) Toxicol. Lett. 112–113:467–471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00-02 from the National Institute of Environmental Health Sciences, released Feb. 29, 2000, available at http://www.niehs.nih.gov/oc/news/toxchip.htm.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for HPDE to quantify the levels of HPDE expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103–111; Mendoze, L. G. et al. (1999) Biotechniques 27:778–788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533–537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150–2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding HPDE may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353–7357.)

Fluorescent in situ hybridization (FISH) may be correlated with other physical and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) World Wide Web site. Correlation between the location of the gene encoding HPDE on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the instant invention may also be used to detect differences in the chromosomal location due to translocation, inversion, etc., among normal, carrier, or affected individuals.

In another embodiment of the invention, HPDE, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HPDE and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with HPDE, or fragments thereof, and washed. Bound HPDE is then detected by methods well known in the art. Purified HPDE can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HPDE specifically compete with a test compound for binding HPDE. In this manner, antibodies can be used to detect the presence of any peptide which shares one or more antigenic determinants with HPDE.

In additional embodiments, the nucleotide sequences which encode HPDE may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications and publications, mentioned above and below, in particular U.S. Ser. No. 60/178,570, U.S. Ser. No. 60/182,042, and U.S. Ser. No. 60/183,178, are expressly incorporated by reference herein.

EXAMPLES

I. Construction of cDNA Libraries

Incyte cDNAs were derived from cDNA libraries described in the LIFESEQ GOLD database (Incyte Genomics, Palo Alto Calif.) and shown in Table 4, column 5. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+ RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), PBK-CMV plasmid (Stratagene), or pINCY (Incyte Genomics, Palo Alto Calif.), or derivatives thereof. Recombinant plasmids were transformed into competent E. coli cells including XL1-Blue, XL 1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM, and hidden Markov model (HMM)-based protein family databases such as PFAM. (HMM is a probabilistic approach which analyzes consensus primary structures of gene families. See, for example, Eddy, S.R. (1996) Curr. Opin. Struct. Biol. 6:361–365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The full length polynucleotide sequences were translated to derive the corresponding full length polypeptide sequences. Alternatively, a polypeptide of the invention may begin at any of the methionine residues of the full length translated polypeptide. Full length polypeptide sequences were subsequently analyzed by querying against databases such as the GenBank protein databases (genpept), SwissProt, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:4–6. Fragments from about 20 to about 4000 nucleotides which are useful in hybridization and amplification technologies are described in Table 4, column 4.

IV. Identification and Editing of Coding Sequences from Genomic DNA

Putative phosphodiesterases were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78–94, and Burge, C. and S. Karlin (1998) Curr. Opin. Struct. Biol. 8:346–354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode phosphodiesterases, the encoded polypeptides were analyzed by querying against PFAM models for phosphodiesterases. Potential phosphodiesterases were also identified by homology to Incyte cDNA sequences that had been annotated as phosphodiesterases. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited or unedited Genscan-predicted coding sequences.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of HPDE Encoding Polynucleotides

The sequences which were used to assemble SEQ ID NO:4–6 were compared with sequences from the Incyte LIFESEQ database and public domain databases using BLAST and other implementations of the Smith-Waterman algorithm. Sequences from these databases that matched SEQ ID NO:4–6 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, or human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (http://www.ncbi.nlm.nih.gov/genemap/), can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{\text{BLAST Score} \times \text{Percent Identity}}{5 \times \text{minimum}\{\text{length}(Seq.\ 1),\ \text{length}(Seq.\ 2)\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding HPDE are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/ condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding HPDE. cDNA sequences and cDNA library/tissue information are found in the LIFESEQ GOLD database (Incyte Genomics, Palo Alto Calif.).

VIII. Extension of HPDE Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 µl PICOGREEN quantitation reagent (0.25% (v/v) PICOGREEN; Molecular Probes, Eugene Oreg.) dissolved in 1×TE and 0.5 µl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent *E. coli* cells. Transformed cells were selected on antibiotic-containing media, and individual colonies were picked and cultured overnight at 37° C. in 384 well plates in LB/2×carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Applied Biosystems).

In like manner, full length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:4–6 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1×saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, supra.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:467–470; Shalon, D. et al. (1996) Genome Res. 6:639–645; Marshall, A. and J. Hodgson (1998) Nat. Biotechnol. 16:27–31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly(A)$^+$ RNA sample is reverse transcribed using MMLV reverse-transcriptase, 0.05 pg/µl oligo-(dT) primer (21mer), 1× first strand buffer, 0.03 units/µl RNase inhibitor, 500 µM dATP, 500 µM dGTP, 500 µM dTTP, 40 µM dCTP, 40 µM dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 µl 5×SSC/0.2% SDS Microarray Preparation Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1–2 ng to a final quantity greater than 5 µg. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 µl of the array element DNA, at an average concentration of 100 ng/µl, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 µl of sample mixture consisting of 0.2 µg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the HPDE-encoding sequences, or any parts thereof, are used to detect, decrease, or inhibit expression of naturally occurring HPDE. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HPDE. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HPDE-encoding transcript.

XII. Expression of HPDE

Expression and purification of HPDE is achieved using bacterial or virus-based expression systems. For expression of HPDE in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HPDE upon induction with isopropyl beta-D-thiogalactopyranoside (IPTG). Expression of HPDE in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HPDE by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, HPDE is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from HPDE at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch. 10 and 16). Purified HPDE obtained by these methods can be used directly in the assays shown in Examples XVI, XVII, and XVIII, where applicable.

XIII. Functional Assays

HPDE function is assessed by expressing the sequences encoding HPDE at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cytomegalovirus promoter. 5–10 µg of recombinant vector are transiently transfected into a human cell line, for example, an endothelial or hematopoictic cell line, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HPDE on gene expression can be assessed using highly purified populations of cells transfected with sequences encoding HPDE and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HPDE and other genes of interest can be analyzed by northern analysis or microarray techniques.

XIV. Production of HPDE Specific Antibodies

HPDE substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the HPDE amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide and anti-HPDE activity by, for example, binding the peptide or HPDE to a substrate, blocking with 1% BSA, reacting with rabbit antisera, washing, and reacting with radio-iodinated goat anti-rabbit IgG.

XV. Purification of Naturally Occurring HPDE Using Specific Antibodies

Naturally occurring or recombinant HPDE is substantially purified by immunoaffinity chromatography using antibodies specific for HPDE. An immunoaffinity column is constructed by covalently coupling anti-HPDE antibody to an activated chromatographic resin, such as CNBr-activated SEPHAROSE (Amersham Pharmacia Biotech). After the coupling, the resin is blocked and washed according to the manufacturer's instructions.

Media containing HPDE are passed over the immunoaffinity column, and the column is washed under conditions that allow the preferential absorbance of HPDE (e.g., high ionic strength buffers in the presence of detergent). The column is eluted under conditions that disrupt antibody/HPDE binding (e.g., a buffer of pH 2 to pH 3, or a high concentration of a chaotrope, such as urea or thiocyanate ion), and HPDE is collected.

XVI. Identification of Molecules Which Interact with HPDE

HPDE, or biologically active fragments thereof, are labeled with $^{125}$I Bolton-Hunter reagent. (See, e.g., Bolton A. E. and W. M. Hunter (1973) Biochem. J. 133:529–539.) Candidate molecules previously arrayed in the wells of a multi-well plate are incubated with the labeled HPDE, washed, and any wells with labeled HPDE complex are assayed. Data obtained using different concentrations of HPDE are used to calculate values for the number, affinity, and association of HPDE with the candidate molecules.

Alternatively, molecules interacting with HPDE are analyzed using the yeast two-hybrid system as described in Fields, S. and O. Song (1989) Nature 340:245–246, or using commercially available kits based on the two-hybrid system, such as the MATCHMAKER system (Clontech).

HPDE may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVII. Demonstration of HPDE Activity

In general, PDE activity of HPDE is measured by monitoring the conversion of a cyclic nucleotide (either cAMP or cGMP) to its nucleotide monophosphate. The use of tritium-containing substrates such as $^3$H-cAMP and $^3$H-cGMP, and 5' nucleotidase from snake venom, allows the PDE reaction to be followed using a scintillation counter.

cAMP-specific PDE activity of HPDE is assayed by measuring the conversion of $^3$H-cAMP to $^3$H-adenosine in the presence of HPDE and 5' nucleotidase. A one-step assay is run using a 100 μl reaction containing 50 mM Tris-HCl pH 7.5, 10 mM MgCl$_2$, 0.1 unit 5' nucleotidase (from *Crotalus atrox* venom), 0.0062–0.1 μM $^3$H-cAMP, and various concentrations of cAMP (0.0062–3 mM). The reaction is started by the addition of 25 μl of diluted enzyme supernatant. Reactions are run directly in mini Poly-Q scintillation vials (Beckman Instruments, Fullerton Calif.). Assays are incubated at 37° C. for a time period that would give less than 15% cAMP hydrolysis to avoid non-linearity associated with product inhibition. The reaction is stopped by the addition of 1 ml of Dowex (Dow Chemical, Midland Mich.) AG1×8 (Cl form) resin (1:3 slurry). Three ml of scintillation fluid are added, and the vials are mixed. The resin in the vials is allowed to settle for one hour before counting. Soluble radioactivity associated with $^3$H-adenosine is quantitated using a beta scintillation counter. The amount of radioactivity recovered is proportional to the cAMP-specific PDE activity of HPDE in the reaction. For inhibitor or agonist studies, reactions are carried out under the conditions described above, with the addition of 1% DMSO, 50 nM cAMP, and various concentrations of the inhibitor or agonist. Control reactions are carried out with all reagents except for the enzyme aliquot.

cGMP-specific PDE activity of HPDE is assayed by measuring the conversion of $^3$H-cGMP to $^3$H-guanosine in the presence of HPDE and 5' nucleotidase. A one-step assay is run using a 100 μl reaction containing 50 mM Tris-HCl pH 7.5, 10 mM MgCl$_2$, 0.1 unit 5' nucleotidase (from *Crotalus atrox* venom), and 0.0064–2.0 μM $^3$H-cGMP. The reaction is started by the addition of 25 μl of diluted enzyme supernatant. Reactions are run directly in mini Poly-Q scintillation vials (Beckman Instruments). Assays are incubated at 37° C. for a time period that would yield less than 15% cGMP hydrolysis in order to avoid non-linearity associated with product inhibition. The reaction is stopped by the addition of 1 ml of Dowex (Dow Chemical, Midland Mich.) AG1×8 (Cl form) resin (1:3 slurry). Three ml of scintillation fluid are added, and the vials are mixed. The resin in the vials is allowed to settle for one hour before counting. Soluble radioactivity associated with $^3$H-guanosine is quantitated using a beta scintillation counter. The amount of radioactivity recovered is proportional to the cGMP-specific PDE activity of HPDE in the reaction. For inhibitor or agonist studies, reactions are carried out under the conditions described above, with the addition of 1% DMSO, 50 nM cGMP, and various concentrations of the inhibitor or agonist. Control reactions are carried out with all reagents except for the enzyme aliquot.

Glycerophosphoryl diester phosphodiesterase activity of HPDE is measured by a coupled spectrophotometric assay utilizing sn-glycerol-3-phosphate dehydrogenase and NAD (Larson, T. J. et al. (1983) J. Biol. Chem. 248:5428–5432; Cameron, C. E. et al. (1998) Infect. Immun. 66:5763–5770). HPDE is assayed at 25° C. in a 0.5 ml assay mixture containing 0.45 ml of 1 M hydrazine-glycine (pH 9.0) buffer, 0.5 M NAD, 10 mM CaCl$_2$, 20 units of glycerol-3-phosphate dehydrogenase (Sigma, St. Louis Mo.), and 0.5 mM glycerophosphorylcholine. Phosphodiesterase activity is monitored spectrophotometrically at 340 nm using a molar absorbance coefficient of 6300 $M^{-1}$ $cm^{-1}$ for NADH. Glycerophosphoryl diester phosphodiesterase activity is proportional to the reduction of NAD.

XVII. Identification of Phosphodiesterase Inhibitors and Agonists

In general, inhibitors and agonists of PDE activity of HPDE can be obtained by screening compounds using the PDE activity assays described in Example XVII. Enzyme assays are carried out in both the presence and absence of a candidate compound, and an inhibitor compound is identified when inhibition of PDE activity of HPDE is observed. Alternatively, an agonist compound is identified when increased PDE activity of HPDE is observed.

A high-throughput screen for inhibitors of cAMP-specific PDE activity of HPDE uses microtiter plate-based scintillation proximity assay (Bardelle, C. et al. (1999) Anal. Biochem. 275:148–155). Purified enzyme is diluted in assay buffer containing 25 mM Hepes-NaOH, 1 mM $MgCl_2$, 0.1 mM EGTA, and 0.1% BSA, pH 7.45, at 20° C. A 1% (w/v) suspension of yttrium silicate beads in 18 mM $ZnSO_4$ is prepared, and dispensed into a microtiter plate in 25 µl aliquots. A reaction is initiated by mixing 50 µl of the diluted enzyme solution with 50 µl of the assay buffer containing 2 µM cAMP and 1.8 µCi ($4 \times 10^6$ dpm) $^3$H-cAMP/ml. After 15 minutes, a reaction is quenched by heating to 95° C. for 2 minutes and then cooled, and 50 µl of this quenched solution is added to a pre-plated aliquot of the yttrium silicate beads. Alternatively, the reaction is not quenched, and 50 µl of the reaction mixture is added directly to the pre-plated beads. The beads are allowed to settle, the microtiter plate is sealed, and the reaction mixtures are measured using a scintillation counter.

Candidate inhibitor compounds are added to individual reaction mixtures to screen for inhibition of PDE activity. Candidate inhibitor molecules may be selected from known PDE inhibitors, modified PDE inhibitors, peptide libraries, chemical libraries, and combinatorial chemical libraries. Inhibitors of cGMP-specific PDE activity of HPDE can be identified by using the above high-throughput screen with guanosine substrates instead of adenosine substrates. Agonists of PDE activity of HPDE can be identified by using the above high-throughput screen and monitoring for increased PDE activity instead of decreased PDE activity. Candidate agonist molecules may be selected from known PDE agonists, modified PDE agonists, peptide libraries, chemical libraries, and combinatorial chemical libraries.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Polypeptide SEQ ID NO: | Incyte Polypeptide ID | Polynucleotide SEQ ID NO: | Incyte Polynucleotide ID |
|---|---|---|---|---|
| 647189 | 1 | 647189CD1 | 4 | 647189CB1 |
| 286210 | 2 | 286210CD1 | 5 | 286210CB1 |
| 1700830 | 3 | 1700830CD1 | 6 | 1700830CB1 |

TABLE 2

| Polypeptide SEQ ID NO: | Incyte Polypeptide ID | GenBank ID NO: | Probability Score | GenBank Homolog |
|---|---|---|---|---|
| 1 | 647189CD1 | g9453796 | 3.00E−63 | dJ131F15.2 (phosphodiesterase I/nucleotide pyrophosphatase 1 (homologous to mouse Ly-41 antigen) (PC1, NPPS)) [*Homo sapiens*] |
| 2 | 286210CD1 | g9948389 | 2.00E−14 | Probable glycerophosphoryl diester phosphodiesterase [*Pseudomonas aeruginosa*] |
| 3 | 1700830CD1 | g6459876 | 7.00E−15 | Glycerophosphoryl diester phosphodiesterase [*Deinococcus radiodurans*] |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 647189CD1 | 477 | S162 T175 S209 T262 T2 S419 Y255 | N101 N158 N292 N329 N362 N369 N382 N389 | Signal peptide: M1-Q24 | MOTIFS HMMER |
| | | | | | Signal peptide: M1-S22 | SPScan |
| | | | | | Transmembrane domains: I6-L23, Y431-F451 | HMMER |
| | | | | | Type I phosphodiesterase: F5-E366 | HMMER-PFAM |
| | | | | | Phosphodiesterase: | BLAST- |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 2 | 286210CD1 | 486 | S128 T159 S301 T423 S484 T164 S424 S33 T164 S208 S210 S222 S318 T479 Y138 | N182 N217 N233 N255 N329 N462 | PD003227: V30-E276 Somatomedin B: DM02434\|P22413\|1-517: L31-Y374 DM02434\|A57080\|6-517: D26-Y374 DM02434\|A55144\|1-561: V30-W139 DM02434\|P39997\|1-469: L31-T242 Transmembrane domain: M380-W401 Protein phosphodiesterase: PD01922A: K108-P118 PD01922B: P122-D157 Protein hydrolase, phosphodiesterase: PD002136: L111-P248 | PRODOM BLAST-DOMO MOTIFS HMMER BLIMPS-PRODOM BLAST-PRODOM |
| 3 | 1700830CD1 | 318 | S85 S283 T31 T36 S128 S179 | N235 | Signal peptide: M1-G13 Protein phosphodiesterase: PD01922A: R38-S48 PD01922B: L52-D87 | MOTIFS SPScan BLIMPS-PRODOM |

TABLE 4

| Polynucleotide SEQ ID NO: | Incyte Polynucleotide ID | Sequence Length | Selected Fragments | Sequence Fragments | 5' Position | 3' Position |
|---|---|---|---|---|---|---|
| 4 | 647189CB1 | 2530 | 1–1085, 1–269, 877–1085 | 3490552F6 (EPIGNOT01) | 505 | 1203 |
| | | | | 2786107F6 (BRSTNOT13) | 1491 | 2016 |
| | | | | 6777323H1 (OVARDIR01) | 1 | 542 |
| | | | | 3490552T6 (EPIGNOT01) | 1815 | 2530 |
| | | | | 6777323J1 (OVARDIR01) | 1116 | 1817 |
| | | | | 3702869F6 (PENCNOT07) | 652 | 1215 |
| 5 | 286210CB1 | 2447 | 1–675, 788–814 | 6340289H1 (BRANDIN01) | 1375 | 1978 |
| | | | | 2697392F6 (UTRSNOT12) | 1 | 581 |
| | | | | 6334237H1 (BRANDIN01) | 1413 | 2004 |
| | | | | 6332977H1 (BRANDIN01) | 1896 | 2447 |
| | | | | 1004764R6 (BRSTNOT03) | 521 | 1305 |
| | | | | 70313183D1 | 798 | 1402 |
| 6 | 1700830CB1 | 1177 | 1077–1177 | 70695293V1 | 614 | 1177 |
| | | | | 70692807V1 | 1 | 632 |

TABLE 5

| Polynucleotide SEQ ID NO: | Incyte Project ID | Representative Library |
|---|---|---|
| 4 | 647189CB1 | BRAPNOT04 |
| 5 | 286210CB1 | BRANDIN01 |
| 6 | 1700830CB1 | BLADTUT05 |

TABLE 6

| Library | Vector | Library Description |
|---|---|---|
| BLADTUT05 | pINCY | Library was constructed using RNA isolated from bladder tumor tissue removed from a 66-year-old Caucasian male during a radical prostatectomy, radical cystectomy, and urinary diversion. Pathology indicated grade 3 transitional cell carcinoma on the anterior wall of the bladder. Patient history included lung neoplasm and tobacco abuse in remission. Family history included malignant breast neoplasm, tuberculosis, cerebrovascular disease, atherosclerotic coronary artery disease, and lung cancer. |
| BRANDIN01 | pINCY | This normalized pineal gland tissue library was constructed from 4 × 10e5 independent clones from a pineal gland tissue library from two different donors. Starting RNA was made from pooled pineal gland tissue removed from two Caucasian females: a 68-year-old (donor A) who died from congestive heart failure and a 79-year-old (donor B) who died from pneumonia. Neuropathology for donor A indicated mild to moderate Alzheimer disease, atherosclerosis, and multiple infarctions. Neuropathology for donor B indicated severe |

TABLE 6-continued

| Library | Vector | Library Description |
|---|---|---|
| | | Alzheimer disease, arteriolosclerosis, cerebral amyloid angiopathy and multiple infarctions. There were diffuse and neuritic amyloid plaques and neurofibrillary tangles throughout the brain sections examined in both donors. Patient history included diabetes mellitus, rheumatoid arthritis, hyperthyroidism, amyloid heart disease, and dementia in donor A; and pseudophakia, gastritis with bleeding, glaucoma, peripheral vascular disease, COPD, delayed onset tonic/clonic seizures, and transient ischemic attack in donor B. The library was normalized in one round using conditions adapted from Soares et al. (1994) Proc. Natl. Acad. Sci. USA 91:9228–9232 and Bonaldo et al. (1996) Genome Res. 6:791, except that a significantly longer (48 hours/round) reannealing hybridization was used. |
| BRAPNOT04 | pINCY | Library was constructed using RNA isolated from pons tissue removed from the brain of a 35-year-old Caucasian male who died from cardiac failure. Pathology indicated moderate leptomeningeal fibrosis and multiple microinfarctions of the cerebral neocortex. Microscopically, the cerebral hemisphere revealed moderate fibrosis of the leptomeninges with focal calcifications. There was evidence of shrunken and slightly eosinophilic pyramidal neurons throughout the cerebral hemispheres. There were also multiple small microscopic areas of cavitation with surrounding gliosis scattered throughout the cerebral cortex. Patient history included dilated cardiomyopathy, congestive heart failure, cardiomegaly, and an enlarged spleen and liver. Patient medications included simethicone, Lasix, Digoxin, Colace, Zantac, captopril, and Vasotec. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/ PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI Auto-Assembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25:3389–3402. | ESTs: Probability value = 1.0E–8 or less Full Length sequences: Probability value = 1.0E–10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85:2444–2448; Pearson, W. R. (1990) Methods Enzymol. 183:63–98; and Smith, T. F. and M. S. Waterman (1981) Adv. Appl. Math. 2:482–489. | ESTs: fasta E value = 1.06E–6 Assembled ESTs: fasta Identity = 95% or greater and Match length = 200 bases or greater; fastx E value = 1.0E–8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19:6565–6572; Henikoff, J. G. and S. Henikoff (1996) Methods Enzymol. 266:88–105; and Attwood, T. K. et al. (1997) J. Chem. Inf. Comput. Sci. 37:417–424. | Probability value = 1.0E–3 or less |
| HMMER | An algorithm for searching a query sequence against hidden Markov model (HMM)-based databases of protein family consensus sequences, such as PFAM. | Krogh, A. et al. (1994) J. Mol. Biol., 235:1501–1531; Sonnhammer, E. L. L. et al. (1988) Nucleic Acids Res. 26:320–322; Durbin, R. et al. (1998) Our World View, in a Nutshell, Cambridge Univ. Press, pp. 1–350. | PFAM hits: Probability value = 1.0E–3 or less Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4:61–66; Gribskov, M. et al. (1989) Methods Enzymol. 183:146–159; Bairoch, A. et al. (1997) Nucleic Acids Res. 25:217–221. | Normalized quality score ≧ GCG-specified "HIGH" value for that particular Prosite motif. Generally, score = 1.4–2.1. |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies. | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12:431–439. | Score = 3.5 or greater |

TABLE 7-continued

| Program | Description | Reference | Parameter Threshold |
|---|---|---|---|
| TMAP | A program that uses weight matrices to delineate transmembrane segments on protein sequences and determine orientation. | Persson, B. and P. Argos (1994) J. Mol. Biol. 237:182–192; Persson, B. and P. Argos (1996) Protein Sci. 5:363–371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. on Intelligent Systems for Mol. Biol., Glasgow et al., eds., The Am. Assoc. for Artificial Intelligence Press, Menlo Park, CA, pp. 175–182. | |
| Motifs | A program that searches amino acid sequences for patterns that matched those defined in Prosite. | Bairoch, A. et al. (1997) Nucleic Acids Res. 25:217–221; Wisconsin Package Program Manual, version 9, page M51–59, Genetics Computer Group, Madison, WI. | |

What is claimed is:

1. An isolated polypeptide comprising the full-length amino acid sequence depicted in SEQ ID NO: 1.

2. An isolated polynueleotide encoding a polypeptide of claim 1.

3. A recombinant polynucleotide comprising a promoter sequence operably linked to a polynucleotide of claim 2.

4. A cell transformed with a recombinant polynucleotide of claim 3.

5. A method for producing a polypeptide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1, and
   b) recovering the polypeptide so expressed.

6. An isolated polynucleotide selected from the group consisting of:
   a) a polynucleotide comprising the polynucleotide sequence of SEQ ID NO:4,
   b) a polynucleotide comprising a naturally occurring polynucleotide sequence having at least 98% sequence identity to the polynucleotide sequence of SEQ ID NO:4, wherein said polynucleotide encodes a polypeptide having phosphodiesterase activity,
   c) a polynucleotide complementary to a), or
   d) a polynucleotide complementary to b), and
   e) an RNA equivalent of a)–d).

7. A composition comprising an effective amount of a polypeptide of claim 1 and a pharmaceutically acceptable excipient.

8. A microarray wherein at least one element of the microarray is a polynucleotide of claim 2.

9. A method of generating an expression profile of a sample which contains polynucleotides, the method comprising:
   a) labeling the polynucleotides of the sample,
   b) contacting the elements of the microarray of claim 8 with the labeled polynucleotides of the sample under conditions suitable for the formation of a hybridization complex, and
   c) quantifying the expression of the polynucleotides in the sample.

10. A method for screening a compound for effectiveness as an agonist of a polypeptide according to claim 1, the method comprising:
    a) contacting a sample comprising a polypeptide according to claim 1 with a compound; and
    b) detecting, if present, any agonist activity in the sample.

11. A method for screening a compound for effectiveness as an antagonist of a polypeptide according to claim 1, the method comprising:
    a) contacting a sample comprising a polypeptide according to claim 1 with a compound; and
    b) detecting, if present, any antagonist activity in the sample.

12. An isolated polypeptide consisting of the amino acid sequence of SEQ ID NO: 1.

* * * * *

SEQUENCE LISTING

<160> NUMBER OF SEQ ID NOS: 6

<210> SEQ ID NO 1
<211> LENGTH: 477
<212> TYPE: PRT
<213> ORGANISM: Homo sapiens
<220> FEATURE:
<221> NAME/KEY: misc_feature
<223> OTHER INFORMATION: Incyte ID No: 647189CD1

<400> SEQUENCE: 1

```
Met Thr Ser Lys Phe Ile Leu Val Ser Phe Ile Leu Ala Ala Leu
 1               5                  10                  15

Ser Leu Ser Thr Thr Phe Ser Leu Gln Pro Asp Gln Gln Lys Val
                20                  25                  30

Leu Leu Val Ser Phe Asp Gly Phe Arg Trp Asp Tyr Leu Tyr Lys
                35                  40                  45

Val Pro Thr Pro His Phe His Tyr Ile Met Lys Tyr Gly Val His
                50                  55                  60

Val Lys Gln Val Thr Asn Val Phe Ile Thr Lys Thr Tyr Pro Asn
                65                  70                  75

His Tyr Thr Leu Val Thr Gly Leu Phe Ala Glu Asn His Gly Ile
                80                  85                  90

Val Ala Asn Asp Met Phe Asp Pro Ile Arg Asn Lys Ser Phe Ser
                95                  100                 105

Leu Asp His Met Asn Ile Tyr Asp Ser Lys Phe Trp Glu Glu Ala
                110                 115                 120

Thr Pro Ile Trp Ile Thr Asn Gln Arg Ala Gly His Thr Ser Gly
                125                 130                 135

Ala Ala Met Trp Pro Gly Thr Asp Val Lys Ile His Lys Arg Phe
                140                 145                 150

Pro Thr His Tyr Met Pro Tyr Asn Glu Ser Val Ser Phe Glu Asp
                155                 160                 165

Arg Val Ala Lys Ile Ile Glu Trp Phe Thr Ser Lys Glu Pro Ile
                170                 175                 180

Asn Leu Gly Leu Leu Tyr Trp Glu Asp Pro Asp Asp Met Gly His
                185                 190                 195

His Leu Gly Pro Asp Ser Pro Leu Met Gly Pro Val Ile Ser Asp
                200                 205                 210

Ile Asp Lys Lys Leu Gly Tyr Leu Ile Gln Met Leu Lys Lys Ala
                215                 220                 225
```

```
Lys Leu Trp Asn Thr Leu Asn Leu Ile Ile Thr Ser Asp His Gly
                230                 235                 240

Met Thr Gln Cys Ser Glu Glu Arg Leu Ile Glu Leu Asp Gln Tyr
                245                 250                 255

Leu Asp Lys Asp His Tyr Thr Leu Ile Asp Gln Ser Pro Val Ala
                260                 265                 270

Ala Ile Leu Pro Lys Glu Gly Lys Phe Asp Glu Val Tyr Glu Ala
                275                 280                 285

Leu Thr His Ala His Pro Asn Leu Thr Val Tyr Lys Lys Glu Asp
                290                 295                 300

Val Pro Glu Arg Trp His Tyr Lys Tyr Asn Ser Arg Ile Gln Pro
                305                 310                 315

Ile Ile Ala Val Ala Asp Glu Gly Trp His Ile Leu Gln Asn Lys
                320                 325                 330

Ser Asp Asp Phe Leu Leu Gly Asn His Gly Tyr Asp Asn Ala Leu
                335                 340                 345

Ala Asp Met His Pro Ile Phe Leu Ala His Gly Pro Ala Phe Arg
                350                 355                 360

Lys Asn Phe Ser Lys Glu Ala Met Asn Ser Thr Asp Leu Tyr Pro
                365                 370                 375

Leu Leu Cys His Leu Leu Asn Ile Thr Ala Met Pro His Asn Gly
                380                 385                 390

Ser Phe Trp Asn Val Gln Asp Leu Leu Asn Ser Ala Met Pro Arg
                395                 400                 405

Val Val Pro Tyr Thr Gln Ser Thr Ile Leu Leu Pro Gly Ser Val
                410                 415                 420

Lys Pro Ala Glu Tyr Asp Gln Glu Gly Ser Tyr Pro Tyr Phe Ile
                425                 430                 435

Gly Val Ser Leu Gly Ser Ile Ile Val Ile Val Phe Phe Val Ile
                440                 445                 450

Phe Ile Lys His Leu Ile His Ser Gln Ile Pro Ala Leu Gln Asp
                455                 460                 465

Met His Ala Glu Ile Ala Gln Pro Leu Leu Gln Ala
                470                 475

<210> SEQ ID NO 2
<211> LENGTH: 486
<212> TYPE: PRT
<213> ORGANISM: Homo sapiens
<220> FEATURE:
<221> NAME/KEY: misc_feature
<223> OTHER INFORMATION: Incyte ID No: 286210CD1

<400> SEQUENCE: 2

Met Val Arg His Gln Pro Leu Gln Tyr Tyr Glu Pro Gln Leu Cys
  1               5                  10                  15

Leu Ser Cys Leu Thr Gly Ile Tyr Gly Cys Arg Trp Lys Arg Tyr
                 20                  25                  30

Gln Arg Ser His Asp Asp Thr Thr Pro Gly Thr Ala Pro Phe Leu
                 35                  40                  45

His Val Gly Ala Val Ala Ala Val Thr Met Leu Ser Trp Ile Val
                 50                  55                  60

Ala Gly Gln Phe Ala Arg Ala Glu Arg Thr Ser Ser Gln Val Thr
                 65                  70                  75

Ile Leu Cys Thr Phe Phe Thr Val Val Phe Ala Leu Tyr Leu Ala
```

-continued

```
                  80                  85                  90
Pro Leu Thr Ile Ser Ser Pro Cys Ile Met Glu Lys Lys Asp Leu
                  95                 100                 105
Gly Pro Lys Pro Ala Leu Ile Gly His Arg Gly Ala Pro Met Leu
                 110                 115                 120
Ala Pro Glu His Thr Leu Met Ser Phe Arg Lys Ala Leu Glu Gln
                 125                 130                 135
Lys Leu Tyr Gly Leu Gln Ala Asp Ile Thr Ile Ser Leu Asp Gly
                 140                 145                 150
Val Pro Phe Leu Met His Asp Thr Thr Leu Arg Arg Thr Thr Asn
                 155                 160                 165
Val Glu Glu Glu Phe Pro Glu Leu Ala Arg Arg Pro Ala Ser Met
                 170                 175                 180
Leu Asn Trp Thr Thr Leu Gln Arg Leu Asn Ala Gly Gln Trp Phe
                 185                 190                 195
Leu Lys Thr Asp Pro Phe Trp Thr Ala Ser Ser Leu Ser Pro Ser
                 200                 205                 210
Asp His Arg Glu Ala Gln Asn Gln Ser Ile Cys Ser Leu Ala Glu
                 215                 220                 225
Leu Leu Glu Leu Ala Lys Gly Asn Ala Thr Leu Leu Leu Asn Leu
                 230                 235                 240
Arg Asp Pro Pro Arg Glu His Pro Tyr Arg Ser Ser Phe Ile Asn
                 245                 250                 255
Val Thr Leu Glu Ala Val Leu His Ser Gly Phe Pro Gln His Gln
                 260                 265                 270
Val Met Trp Leu Pro Ser Arg Gln Arg Pro Leu Val Arg Lys Val
                 275                 280                 285
Ala Pro Gly Phe Gln Gln Thr Ser Gly Ser Lys Glu Ala Val Ala
                 290                 295                 300
Ser Leu Arg Arg Gly His Ile Gln Arg Leu Asn Leu Arg Tyr Thr
                 305                 310                 315
Gln Val Ser Arg Gln Glu Leu Arg Asp Tyr Ala Ser Trp Asn Leu
                 320                 325                 330
Ser Val Asn Leu Tyr Thr Val Asn Ala Pro Trp Leu Phe Ser Leu
                 335                 340                 345
Leu Trp Cys Ala Gly Val Pro Ser Val Thr Ser Asp Asn Ser His
                 350                 355                 360
Thr Leu Ser Gln Val Pro Ser Pro Leu Trp Ile Met Pro Pro Asp
                 365                 370                 375
Glu Tyr Cys Leu Met Trp Val Thr Ala Asp Leu Val Ser Phe Thr
                 380                 385                 390
Leu Ile Val Gly Ile Phe Val Leu Gln Lys Trp Arg Leu Gly Gly
                 395                 400                 405
Ile Arg Ser Tyr Asn Pro Glu Gln Ile Met Leu Ser Ala Ala Val
                 410                 415                 420
Arg Arg Thr Ser Arg Asp Val Ser Ile Met Lys Glu Lys Leu Ile
                 425                 430                 435
Phe Ser Glu Ile Ser Asp Gly Val Glu Val Ser Asp Val Leu Ser
                 440                 445                 450
Val Cys Ser Asp Asn Ser Tyr Asp Thr Tyr Ala Asn Ser Thr Ala
                 455                 460                 465
Thr Pro Val Gly Pro Arg Gly Gly Gly Ser His Thr Lys Thr Leu
                 470                 475                 480
```

```
Ile Glu Arg Ser Gly Arg
            485

<210> SEQ ID NO 3
<211> LENGTH: 318
<212> TYPE: PRT
<213> ORGANISM: Homo sapiens
<220> FEATURE:
<221> NAME/KEY: misc_feature
<223> OTHER INFORMATION: Incyte ID No: 1700830CD1

<400> SEQUENCE: 3

Met Ser Leu Leu Leu Tyr Tyr Ala Leu Pro Ser Leu Gly Ser Tyr
  1               5                  10                  15

Ala Met Leu Ser Ile Phe Phe Leu Arg Arg Pro His Leu Leu His
                 20                  25                  30

Thr Pro Arg Ala Pro Thr Phe Arg Ile Arg Leu Gly Ala His Arg
                 35                  40                  45

Gly Gly Ser Gly Glu Leu Leu Glu Asn Thr Met Glu Ala Met Glu
                 50                  55                  60

Asn Ser Met Ala Gln Arg Ser Asp Leu Leu Glu Leu Asp Cys Gln
                 65                  70                  75

Leu Thr Arg Asp Arg Val Val Val Ser His Asp Glu Asn Leu
                 80                  85                  90

Cys Arg Gln Ser Gly Leu Asn Arg Asp Val Gly Ser Leu Asp Phe
                 95                 100                 105

Glu Asp Leu Pro Leu Tyr Lys Glu Lys Leu Glu Val Tyr Phe Ser
                110                 115                 120

Pro Gly His Phe Ala His Gly Ser Asp Arg Arg Met Val Arg Leu
                125                 130                 135

Glu Asp Leu Phe Gln Arg Phe Pro Arg Thr Pro Met Ser Val Glu
                140                 145                 150

Ile Lys Gly Lys Asn Glu Glu Leu Ile Arg Glu Ile Ala Gly Leu
                155                 160                 165

Val Arg Arg Tyr Asp Arg Asn Glu Ile Thr Ile Trp Ala Ser Glu
                170                 175                 180

Lys Ser Ser Val Met Lys Lys Cys Lys Ala Ala Asn Pro Glu Met
                185                 190                 195

Pro Leu Ser Phe Thr Ile Ser Arg Gly Phe Trp Val Leu Leu Ser
                200                 205                 210

Tyr Tyr Leu Gly Leu Leu Pro Phe Ile Pro Ile Pro Glu Lys Phe
                215                 220                 225

Phe Phe Cys Phe Leu Pro Asn Ile Ile Asn Arg Thr Tyr Phe Pro
                230                 235                 240

Phe Ser Cys Ser Cys Leu Asn Gln Leu Leu Ala Val Val Ser Lys
                245                 250                 255

Trp Leu Ile Met Arg Lys Ser Leu Ile Arg His Leu Glu Glu Arg
                260                 265                 270

Gly Val Gln Val Val Phe Trp Cys Leu Asn Glu Glu Ser Asp Phe
                275                 280                 285

Glu Ala Ala Phe Ser Val Gly Ala Thr Gly Val Ile Thr Asp Tyr
                290                 295                 300

Pro Thr Ala Leu Arg His Tyr Leu Asp Asn His Gly Pro Ala Ala
                305                 310                 315

Arg Thr Ser
```

<210> SEQ ID NO 4
<211> LENGTH: 2530
<212> TYPE: DNA
<213> ORGANISM: Homo sapiens
<220> FEATURE:
<221> NAME/KEY: misc_feature
<223> OTHER INFORMATION: Incyte ID No: 647189CB1

<400> SEQUENCE: 4

| | |
|---|---|
| gtgctccgct ccagagttga gcgcaggtga gctcctgcgc gttccggggg cgttcctcca | 60 |
| gtcaccctcc cgccgttacc cgcggcgcgc ccgagggagt ctcctccaga ccctccctcc | 120 |
| cgttgctcca aactaatacg gactgaacgg atcgctgcga ggattatctt acactgaact | 180 |
| gatcaagtac tttgaaaatg acttcgaaat ttatcttggt gtccttcata cttgctgcac | 240 |
| tgagtctttc aaccaccttt tctctccaac cagaccagca aaaggttcta ctagtttctt | 300 |
| ttgatggatt ccgttgggat tacttatata agttccaac gccccatttt cattatatta | 360 |
| tgaaatatgg tgttcacgtg aagcaagtta ctaatgtttt tattacaaaa acctaccta | 420 |
| accattatac tttggtaact ggcctctttg cagagaatca tgggattgtt gcaaatgata | 480 |
| tgtttgatcc tattcggaac aaatctttct ccttggatca catgaatatt tatgattcca | 540 |
| agttttggga agaagcgaca ccaatatgga tcacaaacca gagggcagga catactagtg | 600 |
| gtgcagccat gtggcccgga acagatgtaa aaatacataa gcgctttcct actcattaca | 660 |
| tgccttacaa tgagtcagtt tcatttgaag atagagttgc caaaattatt gaatggttta | 720 |
| cgtcaaaaga gcccataaat cttggtcttc tctattggga agaccctgat gacatgggcc | 780 |
| accatttggg acctgacagt ccgctcatgg ggcctgtcat ttcagatatt gacaagaagt | 840 |
| taggatatct catacaaatg ctgaaaaagg caaagttgtg gaacactctg aacctaatca | 900 |
| tcacaagtga tcatggaatg acgcagtgct ctgaggaaag gttaatagaa cttgaccagt | 960 |
| acctggataa agaccactat accctgattg atcaatctcc agtagcagcc atcttgccaa | 1020 |
| aagaaggtaa atttgatgaa gtctatgaag cactaactca cgctcatcct aatcttactg | 1080 |
| tttacaaaaa agaagacgtt ccagaaaggt ggcattacaa atacaacagt cgaattcaac | 1140 |
| caatcatagc agtggctgat gaagggtggc acatttaca gaataagtca gatgactttc | 1200 |
| tgttaggcaa ccacggttac gataatgcgt tagcagatat gcatccaata ttttttagccc | 1260 |
| atggtcctgc cttcagaaag aatttctcaa aagaagccat gaactccaca gatttgtacc | 1320 |
| cactactatg ccacctcctc aatatcaccg ccatgccaca caatggatca ttctggaatg | 1380 |
| tccaggatct gctcaattca gcaatgccaa gggtggtccc ttatacacag agtactatac | 1440 |
| tcctccctgg tagtgttaaa ccagcagaat atgaccaaga ggggtcatac ccttatttca | 1500 |
| taggggtctc tcttggcagc attatagtga ttgtattttt tgtaattttc attaagcatt | 1560 |
| taattcacag tcaaatacct gccttacaag atatgcatgc tgaaatagct caaccattat | 1620 |
| tacaagccta atgttacttt gaagtggatt tgcatattga agtggagatt ccataattat | 1680 |
| gtcagtgttt aaaggtttca aattctggga aaccagttcc aaacatttgc agaaaccatt | 1740 |
| aagcagttac atatttaggt atacacacac acacacacac acatacacac acacggacca | 1800 |
| aaatacttac acctgcaaag gaataaagat gtgagagtat gtctccattg ttcactgtag | 1860 |
| catagggata gataagatcc tgctttattt ggacttggcg cagataatgt atatatttag | 1920 |
| caactttgca ctatgtaaag taccttatgt attgcacttt aaatttctct cctgatgggt | 1980 |
| actttaattt gaaatgcact ttatgcacag ttatgtctta taacttgatt gaaaatgaca | 2040 |

| acttttttgca cccatgtcac agaatacttg ttacgcattg ttcaaactga aggaaatttc | 2100 |
| taataatccc gaataatgaa cgtagaaatc tatctccata aattgagaga agaagaaggt | 2160 |
| gataagtgtt gaaaattaaa tgtgataacc tttgaacctt gaattttgga gatgtattcc | 2220 |
| caacagcaga atgcaactgt gggcatttct tgtcttattt cttccagag aacgtggttt | 2280 |
| tcatttattt ttccctcaaa agagagtcaa atactgacag attcgttcta aatatattgt | 2340 |
| ttctgtcata aaattattgt gatttcctga tgagtcatat tactgtgatt tcataataa | 2400 |
| tgaagacacc atgaatatac ttttttcta tatagttcag caatggcctg aatagaagca | 2460 |
| accaggcacc atctcagcaa tgttttctct tgtttgtaat tatttgctcc tttgagaatt | 2520 |
| tagcaattac | 2530 |

<210> SEQ ID NO 5
<211> LENGTH: 2447
<212> TYPE: DNA
<213> ORGANISM: Homo sapiens
<220> FEATURE:
<221> NAME/KEY: misc_feature
<223> OTHER INFORMATION: Incyte ID No: 286210CB1

<400> SEQUENCE: 5

| tggacaagac acctccagga gcccagctca cagccaccgg taccttcttc caggacaagc | 60 |
| tgggggcctc catgggcgcc tgagggccag gcgccagggc cgtgggcacg agtatggtga | 120 |
| gacaccagcc cctgcagtac tacgagccac agctgtgcct ctcctgcctc acgggcatct | 180 |
| acggctgccg ttggaagcgc taccagcgct cccatgatga taccacaccg ggcacagcgc | 240 |
| cattcctgca tgtgggggct gtggcagcag tcaccatgct ctcctggatc gtggcaggac | 300 |
| agttcgcccg cgcagagcgg acctcctccc aggtgaccat tctctgtacc ttcttcaccg | 360 |
| tggtgtttgc cctctacctg gcccctctca ccatctcctc tccctgcatc atggagaaga | 420 |
| aagacctcgg ccccaagcct gctctcattg gccaccgcgg ggcccccatg ctggctccag | 480 |
| agcacacgct catgtccttc cggaaggccc tcgagcagaa gctgtacggg ctccaggctg | 540 |
| acattaccat cagcctggac ggcgtgccct tcctcatgca tgacaccacc ctgcggcgca | 600 |
| ccaccaacgt ggaggaggag ttcccggagc tggcccgcag gcctgcctcc atgcttaact | 660 |
| ggaccaccct gcagagactc aacgctggcc agtggttcct gaagactgac cccttctgga | 720 |
| cagccagctc cctgtcaccc tccgaccaca gagaggccca gaaccagtcc atctgcagcc | 780 |
| tggcagagct cctggagctg gccaagggca atgccacact gctgctcaac ctgcgtgacc | 840 |
| cgccccggga gcaccctac cgcagcagtt ttatcaacgt gactctggag gccgtgctgc | 900 |
| actccggctt cccccagcac caggtcatgt ggctgcctag caggcagagg ccctggtgc | 960 |
| ggaaggtggc tcccggcttc aacagacat caggctccaa ggaggcagtc gccagcctgc | 1020 |
| ggagaggcca catccagcgg ctgaacctgc gctacactca ggtgtcccgc caggagctca | 1080 |
| gggactacgc gtcctggaac ctgagtgtga acctctacac agtcaacgca ccgtggctct | 1140 |
| tctccctgct gtggtgtgcg ggggtcccat ccgtcacctc tgcacaactcc cacaccctgt | 1200 |
| cccaggtgcc ttccccctc tggatcatgc cccggacga gtactgtctc atgtgggtca | 1260 |
| ctgccgacct ggtctccttc accctcatcg tgggcatctt cgtgctccag aagtggcgcc | 1320 |
| tgggtggcat acggagctac aaccctgagc agatcatgct gagtgctgcg gtgcgccgga | 1380 |
| ccagccggga cgtcagcatc atgaaggaga agcttatttt ctcagagatc agcgatggtg | 1440 |
| tagaggtctc cgatgtgctc tccgtatgtt cagacaacag ttatgacaca tatgccaaca | 1500 |

-continued

```
gcaccgccac ccctgtgggc ccccgagggg gtggcagcca caccaagacc ctcatagagc    1560
ggagtgggcg ttagctgaag acatgtctgt cccacctgta cctgacacag aagctgggga    1620
gcctaggaga gctggtggaa gtgtgtctga actcggagtg ctctgggagc gggctccaca    1680
gcctccttgt gggctccagc cccttgtcag ccgcagcctc tcttgagggg gactccctgt    1740
cccctgaggc ccagctgggc caggactcca tcctttcaga tgcccctgca ggcctggggc    1800
tccttctggg aagtatgggg cctagggctt ggtccccctc ttctgaggcc ctctcctgta    1860
tcccgacctg gaagctttga tgggtcatgg gccatgccat ccccctgtg gcaatggagt     1920 gtgtggatgc tcacctgtgc catctgtcct cctgtctgtg ccaggaggca cctgagttct    1980
ctgctgttat cctgccccaa gggcctgggc cgagcctcta cctgaagcaa ctctgctctt    2040
cctgtcagtc tcaaagcaca aggaggttca gcccaggagg aagccagctg caatgtggag    2100
acacgtcctc ctccccaacc cacctcatgc caccgccaac cccctgcccc aggagcgggc    2160
ctgagccacg tcccctagga gcagctggag atggccaaaa gagtgagctc aggactactg    2220
gatcccatgc ccaggtgtcc agcagacctc aaggcagaag ggtcacctaa cccaggagtc    2280
cacagactga tgtgacctca ggttcccaca tcagtggcca cagggcaggg cccacctggt    2340
agaagtgttc tggatatggc cagggtgggt gtgtggctaa gtgggcctga acagagggaa    2400
cctagggccc ttggccaatg tgattaaagc tgccatcttg aaaaaaa              2447
```

<210> SEQ ID NO 6
<211> LENGTH: 1177
<212> TYPE: DNA
<213> ORGANISM: Homo sapiens
<220> FEATURE:
<221> NAME/KEY: misc_feature
<223> OTHER INFORMATION: Incyte ID No: 1700830CB1

<400> SEQUENCE: 6

```
ctcgagccgc gcggacggct gagcgtgtgg ctgcaggagc ttctgtggga gtacggtcat      60
gagccttttg ctgtactatg ccctcccttc cctgggcagc tatgccatgc tctccatctt     120
cttcctgcgc cggcctcatc tgctgcacac gcccagggct cccaccttcc gcatccgcct     180
gggggcccac cgaggaggat ctggagagct gctggagaac accatggagg ccatggagaa     240
ctccatggcc cagcgctcgg acctcctgga gctcgactgt cagctgacac gggacagagt     300
ggtggtggtg tcacatgatg agaacctgtg ccgccagtcg ggcctaaaca gggatgtggg     360
cagcctggac ttcgaggacc tgccctcta caaggagaag ctggaggttt acttctctcc      420
aggccacttt gctcacgggt cagaccggcg catggttcgt ctggaggacc tgttccagag     480
gtttccaagg acacccatga gcgtagagat caaagggaag aacgaagagc tcatccgtga     540
gatagcaggc ttggtgagac gctatgaccg taatgaaatc accatctggg cctcggagaa     600
gagctcggtc atgaagaaat gcaaggctgc caaccccgag atgcccctgt ccttcacaat     660
aagccgagga ttctgggtgc tgctttccta ctacctgggg ctgctgccct tcatcccaat     720
ccctgagaag ttcttcttct gcttcctgcc caacatcatc aacaggacct atttcccatt     780
ttcctgctct tgcctgaacc agttattggc tgtggtttcg aaatggctga tcatgaggaa     840
gagtctgatc cgacacttgg aggagcgagg ggtgcaggtg gtcttttggt gccttaatga     900
agagtcggat tttgaagcag ccttcagcgt gggagccact ggcgtcataa cggattatcc     960
cacagccctg cggcactacc tggacaacca tggaccagct gcccgacct cctaagtcca      1020 gaagcctcga ggtctcctgt ttctcttcct gaaaaataaa tatttgcctt tcgagacctc     1080
```

```
ttcttttgca aaatgcaata taaaaagcca ggttagcaat aaacagaaaa caaaagtgag    1140
ggattccttc cgtagggtag tacggtctgg gaagggg                             1177
```